United States Patent [19]

Kim et al.

[11] Patent Number: 5,278,134
[45] Date of Patent: Jan. 11, 1994

[54] HERBICIDAL PYRIDINE DERIVATIVES AND THEIR SALTS OF 3-(AMINOOXOACETYL)-2-(2-IMIDAZOLIN-2-YL)

[75] Inventors: Dae W. Kim; Hae S. Chang; Dong J. Jeon; Jae W. Ryu; In T. Hwang, all of Daejeon, Rep. of Korea

[73] Assignee: Korea Research Institute of Chemical Technology, Daejeon, Rep. of Korea

[21] Appl. No.: 923,906

[22] PCT Filed: Feb. 28, 1991

[86] PCT No.: PCT/KR91/00005
§ 371 Date: Oct. 27, 1992
§ 102(e) Date: Oct. 27, 1992

[30] Foreign Application Priority Data

Feb. 28, 1990 [KR] Rep. of Korea ............. 90-2649

[51] Int. Cl.⁵ ............. A01N 43/40; C07D 401/04
[52] U.S. Cl. ............. 504/253; 504/225; 504/235; 504/209; 504/247; 546/278; 546/167; 540/598; 544/131; 544/360
[58] Field of Search ............. 504/753; 546/278

[56] References Cited

U.S. PATENT DOCUMENTS 4,824,474  4/1989  Numata et al. ............. 71/92
4,851,092  7/1989  Maresch ............. 204/145 R

FOREIGN PATENT DOCUMENTS 0041623  12/1981  European Pat. Off. .
0298029   1/1989  European Pat. Off. .
0322616   7/1989  European Pat. Off. .
2174395  11/1986  United Kingdom .

Primary Examiner—Jane T. Fan
Attorney, Agent, or Firm—Cushman, Darby & Cushman

[57] ABSTRACT

The present invention relates to new 3-(aminooxoacetyl)-2-(2-imidazolin-2-yl)pyridines and their salts, having herbicidal activity.

23 Claims, No Drawings

HERBICIDAL PYRIDINE DERIVATIVES AND THEIR SALTS OF 3-(AMINOOXOACETYL)-2-(2-IMIDAZOLIN-2-YL)

TECHNICAL FIELD

The present invention relates to a novel 3-(aminooxoacetyl)-2-(2-imidazolin-2-yl)pyridine and their salts, having a herbicidal activity.

BACKGROUND ART

The imidazolinone herbicides, a potent class, have publicly known and until recently, British patent No. 2,174,395 discloses the compounds having the following formula (A).

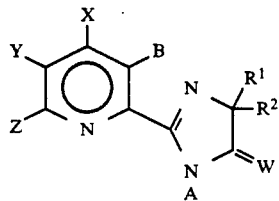

Wherein:
$R^1$ is $C_1$-$C_4$ alkyl;
$R^2$ is $C_1$-$C_4$ alkyl or $C_3$-$C_6$ cycloalkyl;
B is $CO_2R^3$, $CONHR^6$, CHO, $CH_2OH$, $COCH_3$, $COC_6H_5$, CN, $CH_3$, CH=NOH, $CH_2COOH$, CONHOH, CHROH, $CH_2CH_2COOH$,

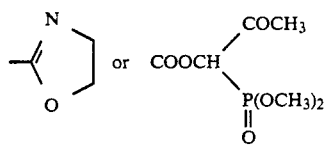

(wherein, $R^3$ is hydrogen, dialkylimino, substituted alkyl, alkenyl or cation, $R^6$ is hydrogen, hydroxy or alkenyl) A is hydrogen, $COR^4$, $SO_2R^5$, etc.

The above patent introduces many a herbicidal compounds, but they have recognized a disadvantage in that except for soybean, such compounds failed to exert an effective selectivity of herbicidal activity as herbicide.

Also, such imidazolinone compounds are specified in the following patents, say, German Patent No. 2,833,274, U.S. Pat. Nos. 4,824,466/4,851,021/4,824,474, European Patent No. 41,623/298,029/322,616.

However, the current situation is that the undesirable vegetation should be controlled so as to improve the growth of useful crops such as corn, rice, cotton, wheat, and soybean. The failure to check the weed growth in such useful crops may bring about significant losses to farmers and to consumer as well. Thus, the continuous research to develop more effective products should be required for a good harvest.

DETAILED DESCRIPTION OF THE INVENTION

The present invention relates to novel compounds demonstrating a herbicidal activity and to agriculturally suitable compositions thereof, and a method of their uses as general and/or selective preemergent and/or postemergent herbicides or plant growth regulants.

More specifically, said compounds demonstrating a herbicidal activity are 3-(aminooxoacetyl)-2-(2-imidazolin-2-yl)pyridine having a following stucture of general formula(I).

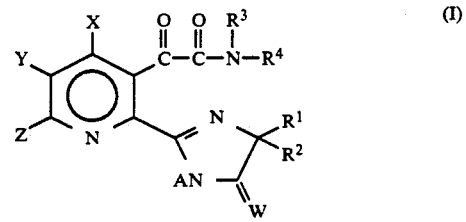

wherein, $R^1$ is $C_1$-$C_4$ alkyl;

$R^2$ is $C_1$-$C_4$ alkyl, $C_3$-$C_5$ cycloalkyl or $C_1$-$C_4$ alkyl optionally substituted with 1-4 fluorine;

$R^3$ is hydrogen, $C_1$-$C_3$ alkyl, $C_1$-$C_3$ alkyl optionally substituted with substituents contained in the following group I, $C_2$-$C_4$ alkenyl or $C_2$-$C_4$ alkynyl;

$R^4$ is the same as $R^3$; or phenyl, benzyl, pyridyl, furanyl, thiophenyl, benzofuranyl, dihydrobenzofuranyl, benzothiophenyl, dihydrobenzothiophenyl, indolyl, indolinyl, optionally substituted with 0-3 same or different substituents selected from the substituents contained in group II ; and when taken together, connecting $R^3$ and $R^4$, a 3-7 membered ring may be formed, which may contain 0-3 double bonds or 0-3 O, N, SOn(n=0-2);

W is O or S;

X is hydrogen, $C_1$-$C_4$ alkyl, $C_1$-$C_4$ alkoxy, $C_1$-$C_4$ alkoxyalkyl, or halogen;

Y, Z are each hydrogen, halogen, $C_1$-$C_6$ alkyl, $C_1$-$C_6$ alkoxy, $C_1$-$C_6$ alkoxyalkyl, $C_1$-$C_6$ alkylthio, phenoxy, $C_1$-$C_6$ haloalkyl, $C_1$-$C_6$ alkylamino, $C_1$-$C_6$ alkylsulfonyl or phenyl optionally substituted with one $C_1$-$C_4$ alkyl, $C_1$-$C_4$ alkoxy or halogen; and when taken together, a 5-6 membered ring may be formed in which may contain O,N,S, double bonds or—$(CH_2)_n$—, (n=0-4);

A is hydrogen or —$COR^5$ (where $R^5$ is hydrogen, methyl or $CH_2Cl$); when A is hydrogen, tautomeric isomer may exist;

Group I contains hydroxy, alkoxy, haloalkoxy, cyano, —$CO_2R^6$ (where $R^6$ is hydrogen, alkyl, alkenyl, or alkynyl), alkylthio, alkylsulfonyl, phenylthio, phenylsulfonyl, haloalkylthio, alkenoxy, alkoxy, —$NR^6R^7$ (where $R^6$, $R^7$ are each hydrogen, alkyl, alkenyl or alkynyl or $R^6$, $R^7$ may form a ring), phenyl, or phenoxy;

Group II contains group I substituents, halogen, nitro, haloalkyl, alkoxyalkyl, alkyl, alkenyl, alkynyl, alkylthioalkyl, —$COR^8$ (where $R^8$ is hydrogen, alkyl or phenyl) —$CO_2R^9$ (where $R^9$ is hydrogen or alkyl), —$SO_3R^{10}$ (where $R^{10}$ is hydrogen or alkyl), —$SO_2NR^6R^7$,—$CONR^6R^7$ ($R^6$,$R^7$ are the same as above), or

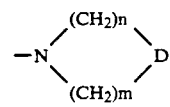

(where n, m are an integer of 1-3, D is a single bond or double bond, O, S, $SO_2$, $NCH_3$).

A preferred group of 3-(aminooxoacetyl)-2-(2-imidazolin-2-yl)pyridine compounds having the formula shown as above(I), wherein $R^1$ is methyl, $R^2$ is methyl, ethyl, isopropyl or cyclopropyl; W is oxygen; A is hydrogen, X is hydrogen, Y, Z is each hydrogen, $C_1$-$C_6$ alkyl or $C_1$-$C_6$ alkoxy, and when Y and Z are taken together, YZ is —(CH$_2$)$_4$, —CH=CH—CH=CH—, or —O(CH$_2$)$_3$—, and $R^3$ is hydrogen or $C_1$-$C_2$ alkyl, $R^4$ is $C_1$-$C_2$ alkyl optionally substituted with 0–2 substituents selected from halogen, hydroxy, alkoxy, alkylthio, amino, phenyl, phenoxy;

$C_2$-$C_6$ alkenyl, $C_2$-$C_6$ alkynyl, or phenyl optionally substituted with 0–3 same or different selected from substituents contained in the above group II, when taken together, connecting $R^3$ and $R^4$, a 3–7 membered ring may be formed, which may contain 0–3 double bonds or 0–3, O, N, SOn(n=0–2);

A more preferred group of 3-(aminooxoacetyl)-2-(2-imidazolin-2-yl)pyridines, wherein A and X is each hydrogen, Y is hydrogen, $C_1$-$C_2$ alkyl or $C_1$-$C_2$ alkoxy, Z is hydrogen, $R^1$ is methyl, $R^2$ is isopropyl, $R^3$ is methyl or ethyl, $R^4$ is benzyl, phenyl, or phenyl substituted with 1–3 substituents selected from $C_1$-$C_6$ alkyl, phenoxy, $C_1$-$C_6$ alkoxy, halogen, haloalkyl, $C_1$-$C_6$ alkylthio, $C_1$-$C_6$ alkylsulfone $C_1$-$C_6$ dialkylamino, or those where —NR$^3$R$^4$ is

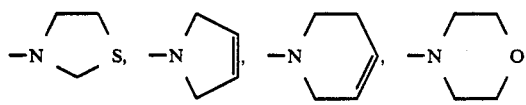

Among the definitions according to the present invention, the following terms have the following meanings:
a) "Alkyl" used either alone or in compound words such as "alkylthio" or "haloalkyl", etc. denotes straight chain, or branched alkyls within six carbon atoms.
b) "Alkenyl" denotes straight chain or branched alkenes within six carbon atoms.
c) "Alkynyl" denotes straight chain or branched alkynes within six carbon atom.
d) "Alkoxy" denotes groups of O-alkyls defined as above.
e) "Halogen" denotes either alone or in compound words such as haloalkyl denotes fluorine, chlorine, or bromine.

As a useful herbicide, said 3-(aminooxoacetyl)-2-(2-imidazolin-2-yl) pyridine compounds and their salts of the present invention may be used in cultivating soybean, corn, wheat, barley, rice, and cotton. The salts of said compounds can be prepared as an acid-addition salt or an alkali, alkaline earth metal or quaternary amine salts.

Compounds of the present invention can be prepared by reactions as described in hereinbelow. The compounds of general formula(I) can be obtained by acylating the compounds of formula(II), when neither of $R^3$ or $R^4$ is hydrogen, can be prepared as shown in Reaction(1)

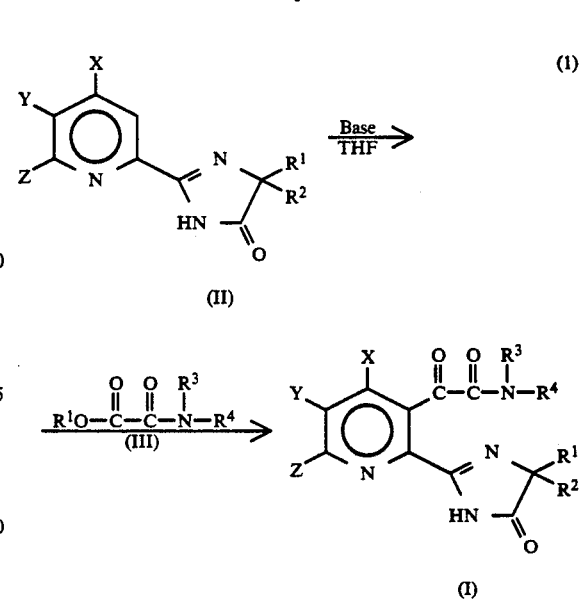

From the above reaction(1), BuLi and LDA are preferably used as a strong base, possibly at the temperature of −78°∼30° C.

The synthesis method in the compound of said general formula(II) is publicly known, and its synthesis is available by Korea Patent Publication No. 85-1817 and Germany Patent DE No.2,833,274/3,121,736.

If $R^3$ is hydrogen, the manufacture of said compound should be preferably made available by protecting this functional group under the following reaction(2).

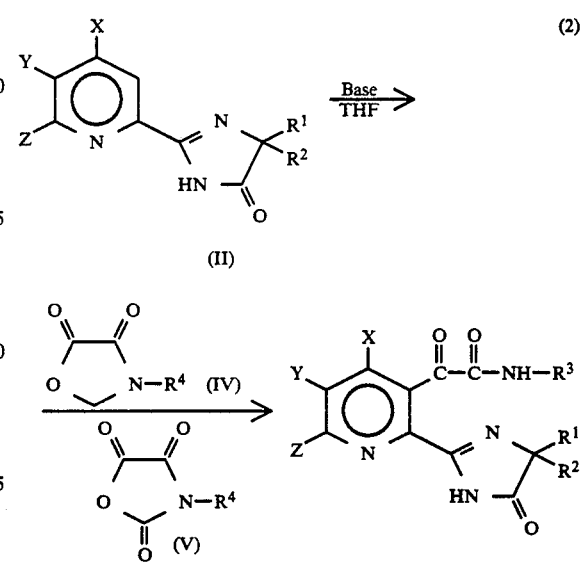

When there is a substituent of hydroxy having active hydrogen in $R^3$ or $R^4$ from the above reaction, the systhesis is made available by protecting the substituent under the reaction(1) or reaction(2).

Also, the novel compound of the present invention may be synthesized by the following reaction(3), wherein n=the fixed number of 1∼6, $R^3$ is hydrogen or has a substituent of hydroxy.

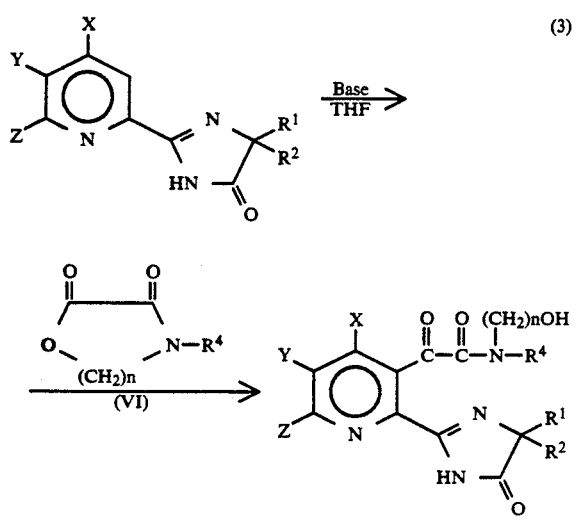

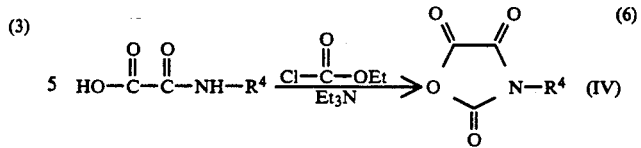

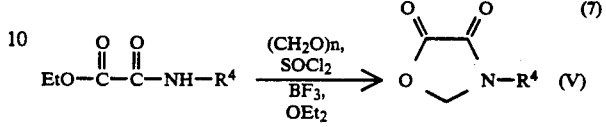

The manufacture of said general formula(VI) may be made available by the existing method, and the manufacture of said general formula(VIII) may be made available by the following reaction(8).

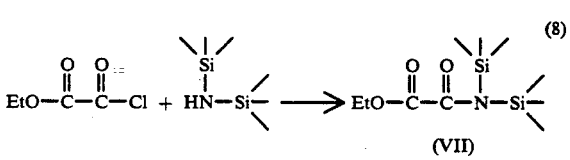

If $R^3$ and $R^4$ is each hydrogen, the manufacture of said compound should be preferably made available by protecting the amino functional group under the following reaction(4).

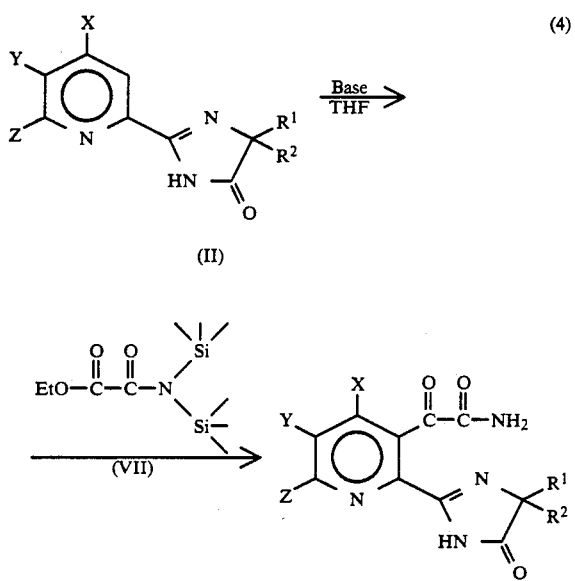

Meantime, the manufacture of general formula(III) used in said reaction(1) may be made available by reacting with oxalic acid ester and amine as do in the following reaction(5).

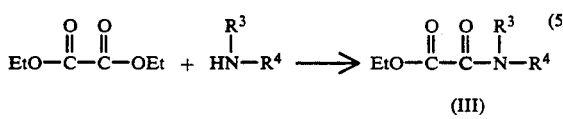

Also, the manufacture of said general formula(IV) and (V) may be made available by the following reaction(6) and (7).

The compounds of said general formula(I) of the present invention specify the following materials:

3-(N-methyl-N-3-fluorophenyl-aminooxoacetyl)-2-(4-isopropyl-4-methyl-5-oxo-2-imidazolin-2 -yl)-5-methylpyridine 3-(N-methyl-N-3-chloro-4-methoxyphenyl-aminooxoacetyl)-2-(4-isopropyl-4-methyl-5-oxo-2 -imidazolin-2-yl)-5-methylpyridine 3-(N-methyl-N-3,5-dimethylphenyl-aminooxoacetyl)-2-(4-isopropyl-4-methyl-5-oxo-2-imidazolin-2 -yl)-5-methylpyridine 3-(N-methyl-N-4-n-butylphenyl-aminooxoacetyl)-2-(4-isopropyl-4-methyl-5-oxo-2-imidazolin-2 -yl)-5-methylpyridine 3-(N-methyl-N-4-t-butylphenyl-aminooxoacetyl)-2-(4-isopropyl-4-methyl-5-oxo-2-imidazolin-2 -yl)-5-methylpyridine 3-(N-methyl-N-4-phenoxyphenyl-aminooxoacetyl)-2-(4-isopropyl-4-methyl-5-oxo-2-imidazolin-2 -yl)-5-methylpyridine 3-(N-methyl-N-3-chlorophenyl-aminooxoacetyl)-2-(4-isopropyl-4-methyl-5-oxo-2-imidazolin-2 -yl)-5-methylpyridine 3-(N-methyl-N-4-cyclohexylphenyl-aminooxoacetyl)-2-(4-isopropyl-4-methyl-5-oxo-2-imidazolin-2 -yl)-5-methylpyridine 3-(N-methyl-N-4-dimethylaminophenyl-aminooxoacetyl)-2-(4-isopropyl-4-methyl-5-oxo-2-imidazolin-2yl)-5-methylpyridine 3-(N-methyl-N-3-trifluoromethylphenyl-aminooxoacetyl)-2-(4-isopropyl-4-methyl-5-oxo-2 -imidazolin-2-yl)-5-methylpyridine 3-(N-methyl-N-3,4-dichlorophenyl-aminooxoacetyl)-2(4-isopropyl-4-methyl-5-oxo-2-imidazolin-2 -yl)-5-methylpyridine 3-(N-methyl-N-4-trifluoromethylphenyl-aminooxoacetyl)-2-(4-isopropyl-4-methyl-5-oxo-2 -imidazolin-2-yl)-5-methylpyridine 3-(N-methyl-N-3-methyphenyl-aminooxoacetyl)-2-(4-isopropyl-4-methyl-5-oxo-2-imidazolin-2-yl )-5-methylpyridine The above-manufactured compounds of said general formula(I) are used, in various forms of solutions and powders having herbicidal compositions, to the soil containing plant's leaf or plant-breeding part. The dosage forms available are wettable powder, flow concentrates, emulsifiable concentrates, and granules.

According to the present invention, the wettable powder is homogeneously dispersed in water; in addition to the active composition, diluent, and non-toxic material, said wettable agent is manufactured by the following materials: polyoxyethylated alkylphenols, polyoxyethylated fatty alcols, alkyl or alkylphenyl sulfonates. The dispersing agent includes sodium lignin sulfonate, sodium 2,2'-dinaphthylmethane-6,6' disulfonate, sodium dibutyl naphthalene sulfonate, or sodium oleil-methyltauride. Such agents are manufactured by the existing method by pulverizing and mixing the ingredients.

The flow concentrates may be manufactured by mixing/melting the active ingredients into non-toxic organic solvent(e.g., butanol, cyclohexanol, DMF, xylene, or high boiling aromatics, or hydrocarbons), together with any one or more emulsifiers.

As an usable emulsifier, calcium alkylsulfonates includes calcium dodesylbenzenesulfonate or non-ionic emulsifier includes fatty acid polyglycolesters, alkylaryl polyglycolethers, fatty alcol polyglycolethers, propyleneoxide, ethyleneoxide polymers, fattyalcohol, propyleneoxide ethyleneoxide polymers, alkylpolyglocolethers, sorbitan fatty acid esters, polyoxyethylene sorbitan fatty acid esters, or polyoxyethylene sorbitol esters.

Also, a powdering agent may be manufactured by pulvering the active ingredient with talc of micropulverized solid and natural clay(e.g., kaolin, bentonite, pyrophilite, or siliceous earth).

And a granular agent may be manufactured either by spraying the active ingredient on inactive adsorbent in granular form or by adsorbing the active flow concentrates on the surface of intermediates, say, sand, kaolinites.

The usable adsorbent includes polyvinyl alcol, sodium polyacrylate or mineral oils.

The herbicides of general formula(I) in the present invention may be manufactured by the existing method of fertilizer-granule agent, and if necessary, they may also be manufactured by the mixture of fertilizer.

The preparations containing aforementioned active ingredients may, if necessary, contain wettable agents, dispersing agents, emulsifiers, impregnating agents, solvents, fillers, intermediates, etc. For the actual appication, the flow concentrates in a commercial form may be used by appropriate dilution.

For example, the wettable powder or emulsifiable concentrates is used by dilution, while powdering/granular/ spraying solution, inactive materials, are not diluted.

Also, the flowable liquid is composed of the following: active ingredient of 30~50 wt %, gelator of 1~3 wt %, dispersing agent of 1~5 wt %, alcohol of 0.1~3 wt %, and water of 40~60 wt %. The prevailing method of manufacturing the flowable liquid is based upon the following formula: in proportion to the active ingredient of about 40 wt %, gelator(e.g., bentonite) of about 2 wt %, dispersing agent(e.g., lignosulfate), polyethylene alcohol of 1 wt %, and water of 54 wt %.

Also, the prevailing method of manufacturing the concentrated emulsifying liquids is based upon the following formula: after dissolving the active ingredient of about 5~25 wt % into N-methylpyrrolidone, isoporone, butylcellosolve, methylacetate in about 65~90 wt %, some non-ionic surfactant(e.g., alkyloxy polyethoxy alcohol) of about 5~10 wt % is dispersed into said liquids. When said concentrated liquids are used, they are dispersed into water to make the spraying solution.

In case the compounds of the present invention are to be used as the herbicide containing a soil-treating agent, they may be used by manufacturing a granular agent; to manufacture said agent, the active ingredient is dissolved into some solvent(e.g., methylene chloride and N-methylpyrrolidone) and said formed solution is sprayed to granular carries such as powder of corn stalk, sand, attapulgite, and kaolin. In general, the above manufactured granular agent contains the active ingredient of about 3~20 wt % and the granular carrier of about 97~80 wt %.

Meantime, the compounds of general formula(I) of the present invention are the most effective herbicide in controlling one-year weed, perenial plant, mono- or bicotyledonous plant.

Also, said compounds is quite effective in eliminating the weeds growing in the dry/humid soil areas only. They are used as underwater herbicides and if said compounds, in a ratio of about 0.06~10 kg/ha, are given to plant's leaves, soil, or the breeding parts such as tuber, rhizome, or ladix, the plant may be eliminated successfully and effectively.

Moreover, surprisingly, it is found that various kinds of compounds of general formula(I) demonstrate their selective herbicidal effect according to the kinds of plant eliminated, when they are given to plant's leaves, or soil, in a low ratio. It is also noted that said compounds may be widely used as pre-emergent or as post-emergent.

However, it does not mean that said compounds of general formula(I) are non-selective. Especially, certain compounds are selective in soybean, wheat, barley, corn, rice, and cotton, while other compounds are said to be effective as growth-inhibitors against plant.

As above, the novel compounds of the present invention may be used not only as effective herbicides, but also as growth-modulators for inhibiting the plant's growth. The applicable amount of said compounds is decided based upon various considerable factors.

For example, the following factors should be considered; kinds of plants, controlled type of weeds, climate, weather, dosage forms, applicable methods, quantity of leaf. A low amount is preferably used in the following cases; a) soil having less content of organic material b) the transformation inplant growth or short-term duration should be required.

The following Examples illustrate ways in which the principle of this invention has been applied, but are not to be construed as limiting its scope.

| | | |
|---|---|---|
| acetochlor | bromacil | clethodim |
| acifluofen | bromoxynil | clomazone |
| acrolein | butachlor | cloproxydim |
| alachlor | buthidazole | clopyralid |
| ametryn | butralin | CMA |
| amitrole | butylate | cyanazine |
| AMS | cacodylic acid | cycloate |
| asulam | CDAA | cycluron |
| atrazine | CDEC | cyperquat |
| barban | chloramben | cyprazine |
| benefin | chlorbromuron | cyprazole |
| bensulfuron methyl | chlorimuron ethyl | cypromid |
| bensulide | chloroxuron | dalapon |

| | -continued | |
|---|---|---|
| bentazon | chlorporpham | dazomet |
| benzofluor | chlorsulfuron | DCPA |
| benzoylprop | chloroluron | desmediphan |
| bifenox | cimmethylin | desmetryn |

EXAMPLE 1

3-(N,N-dimethylaminooxoacetyl)-2-(4-isopropyl-4-methyl-5-oxo-2-imidazolin-2-yl)-5-methyl pyridine To a stirred solution of 2.5 g (0.011 mole) of 2-(5-isopropyl-5-methyl-4-oxo-2-imidazolin-2 -yl)-5-methyl pyridine in 100 ml of dry tetrahydrofuran cooled to −70° C. under the presence of nitrogen was added dropwise a 9.68 ml of 2.5 molar n-butyllithium, thereby temperature was maintained below −65° C. The solution was stirred at −70° C. for 3 hours and a solution 1.96 g of N,N-dimethyl oxamic acid methyl ester(0.015 mole) in 10 ml of anhydrous tetrahydrofuran was added dropwise while maintaining the temperature below −65° C. After stirring another hour at −70° C., the solution was poured into water and extracted with methylene chloride. The combined organic phases were dried over magnesium sulfate, and evaporated under reduced pressure. Trituration of the residue with diethyl ether affored a crude solid which was recrystallized from a mixture of diethyl ether and methylene chloride to yield 1.67 g of a white solid (m.p= 180°-182° C.).

EXAMPLE 2

Preparation of 2-(4-isopropyl-4-methyl-5-oxo-2-imidazolin-2-yl)-5-methyl-3 -(N-methyl-N-phenyl amino oxo acetyl)pyridine To a stirred solution of 2.5 g(0.011 mole) of 2-(5-isopropyl-5-methyl-4-oxo-2-imidazolin-2 -yl)-5-methyl pyridine in 100ml of anhydrous tetrahydrofuran cooled to −70° C. under the presence of nitrogen was added dropwise a 9.68 ml of 2.5 molar n-butyllithium, thus maintaining temperature below −65° C. The solution was stirred at −70° C. for 3 hr and a solution 1.96 g of N-methyl-N-phenyl oxamic acid methyl ester(3.4 g, 0.016 mole) in 10 ml of anhydrous tetrahydrofuran was added dropwise while maintaining temperature below −65° C. After stirring another hour at −70° C., the solution was poured into water and extracted with methylene chloride. The combined organic phases were dried over anhydrous magnesium sulfate, filtered, and concentrated under reduced pressure to give crude product. The crude product was purified by column chromatography to produce 1.76 g of pale yellow solid( m.p.=153°~156° C.).

EXAMPLE 3

Preparation of 2-(4-isopropyl-4-methyl-5-oxo-2-imidazolin-2-yl)-5-methyl-3 -(N-methyl-N-phenyl amino oxo acetyl)pyridine To a stirred solution containing 3.0g(0.13 mole)-2-(5-isopropyl-5-methyl-4-oxo-2-imidazolin-2 -yl)-5-methyl pyridine in 100ml dry THF at −70° C. under nitrogen was added dropwise 12.48 ml of 2.5 molar n-butyllithium in hexane without allowing the temperature to rise above −65° C. The solution was stirred at −70° C. for 3 hours and a solution 2.58 g of 3-methyloxazolin-2,4,5-trione(0.02 mole)in 10 ml dry THF was added dropwise while maintaining the temperature below −65° C. After stirring another hour at −70° C., the reaction mixture was allowed to attain room temperature. Reaction mixture was poured into water, the pH was adjusted to 7 with 5N $H_2SO_4$ and extracted with methylene chloride.

The combined organic phases were dried over anhydrous magnesium sulfate, filtered, and concentrated under reduced pressure to give crude product. The crude product was purified by column chromatography to afford 1.27 g of pale yellow solid(m.p.=174°-178° C.).

The Synthesis of using following compounds based upon said Examples 1~3 was conducted : A-1~A-39 compound as shown in the following general formular (I-A), B-1~B-81 compound as shown in the following general formula (I-B), C-1~C-34 compound as shown in the following general formula(I-C), and D-1~D-6 compound as shown in the following general formular-(I-D).

The herbicidal activity of said compound was measured in the greenhouse test.

TABLE 1

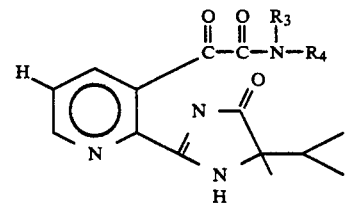

| Compd. No. | K No. | $R_3$<br>$\vert$<br>$N-R_4$ | m.p. (°C.) |
|---|---|---|---|
| A-1 | | $CH_3$<br>$\vert$<br>$N-CH_3$ | 124–127 |
| A-2 | | Et<br>$\vert$<br>N—Et | 156–159 |
| A-3 | | n-Pr<br>$\vert$<br>N-n-Pr | 145–148 |
| A-4 | | 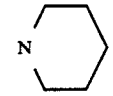 | 179–181 |
| A-5 | | 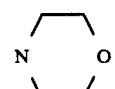 | 216–219 |
| A-6 | | 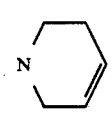 | 188–184 |
| A-7 | | 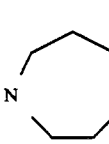 | 150–152 |

TABLE 1-continued

[Structure: pyridine-based compound with R3, R4 substituents on amide]

| Compd. No. | R³—N—R⁴ | m.p. (°C.) |
|---|---|---|
| A-8 | N-methylpiperazinyl | 136–139 |
| A-9 | N(CH₃)CH₂C≡CH | 156–159 |
| A-10 | 2,5-dihydropyrrol-1-yl | 189–193 |
| A-11 | 2,6-dimethylpiperidin-1-yl | 150–153 |
| A-12 | N(CH₃)Ph | 127–129 |
| A-13 | N(CH₃)cyclohexyl | 196–198 |
| A-14 | N(Et)Ph | 174–176 |
| A-15 | N(Et)CH₂Ph | Amorphous Solid |
| A-16 | N(Bu)CH₂Ph | 150–152 |
| A-17 | N(CH₃)(2-CH₃-C₆H₄) with extra CH₃ | 156–158 |
| A-18 | N(Et)(3-CH₃-C₆H₄) | 162–164 |
| A-19 | N(Et)(2,3-diMe-C₆H₃) | 192–194 |

| Compd. No. | K No. | R³—N—R⁴ | m.p. (°C.) |
|---|---|---|---|
| A-20 | | N(Et)(3,5-diMe-C₆H₃) | 207–209 |
| A-21 | | N(Me)(2-OCH₃-C₆H₄) | 95–97 |
| A-22 | | N(CH₃)(3-OCH₃-C₆H₄) | 135–137 |
| A-23 | | N(Me)(4-n-Bu-C₆H₄) | 152–154 |
| A-24 | | N(Me)(4-t-Bu-C₆H₄) | 206–208 |
| A-25 | | N(Me)(4-CH₃O-2-CH₃-C₆H₃) | 145–147 |
| A-26 | | N(Me)(2-Cl-C₆H₄) | 169–170 |
| A-27 | | N(Me)(3-Cl-C₆H₄) | 198–199 |

TABLE 1-continued

[Structure: pyridine with H at position, bearing -C(=O)-C(=O)-N(R3)(R4) group and fused imidazoline ring with t-Bu substituent and NH]

| Compd. No. | R³—N—R⁴ | m.p. (°C.) |
|---|---|---|
| A-28 | MeN-C₆H₄-Cl (4-Cl) | 171-173 |
| A-29 | MeN-C₆H₃(Cl)(OMe) (3-Cl, 4-OMe) | 199-201 |
| A-30 | MeN-C₆H₃(Cl)(CF₃) (2-Cl, 4-CF₃) | 170-172 |
| A-31 | EtN-C₆H₃(CH₃)(F) (2-CH₃, 3-F) | 160-162 |
| A-32 | MeN-C₆H₃(F)(F) (2,4-diF) | 162-164 |
| A-33 | Me-N-C₆H₄-CF₃ (3-CF₃) | 192-194 |
| A-34 | EtN-C₆H₃(methylenedioxy) | 163-165 |
| A-35 | iso-Pr-NH | 200-202 |
| A-36 | t-Bu-NH | Amorphus Solid |
| A-37 | NH—CH₂CH₂Cl | Amorphus Solid |
| A-38 | MeNCH₂CH₂OH | 155-159 |
| A-39 | t-Bu-N—CH₂CH₂OH | 159-163 |

TABLE 2

[Structure: 5-methylpyridine with -C(=O)-C(=O)-N(R3)(R4) group and fused imidazolinone ring with t-Bu substituent]

| Compd. No. | K No. | R³—N—R⁴ | m.p. (°C.) |
|---|---|---|---|
| B-1 | | NH₂ | |
| B-2 | | MeNMe | 185-187 |
| B-3 | | EtNEt | 156-158 |
| B-4 | | n-PrN n-Pr | 102-104 |
| B-5 | | iso-Pr—N-iso-Pr | 210-212 |
| B-6 | | pyrrolidin-1-yl | 207-208 |
| B-7 | | piperidin-1-yl | 188-189 |
| B-8 | | morpholin-4-yl | 206-207 |
| B-9 | | 1,2,3,6-tetrahydropyridin-1-yl | 187-189 |
| B-10 | | azepan-1-yl (hexamethyleneimino) | 164-166 |
| B-11 | | 4-methylpiperazin-1-yl | 183-185 |
| B-12 | | thiomorpholin-4-yl | 175-177 |
| B-13 | | N(CH₂CH=CH₂)₂ (diallylamino) | 227-229 |
| B-14 | | MeN-CH₂C≡CH | 135-137 |
| B-15 | | 2,5-dihydro-1H-pyrrol-1-yl | 217-219 |
| B-16 | | 2,6-dimethylpiperidin-1-yl | 184-187 |

TABLE 2-continued
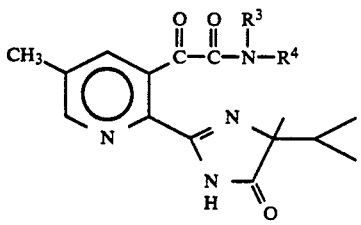
| Compd. No. | K No. | R³—N—R⁴ | m.p. (°C.) |
|---|---|---|---|
| B-17 | | MeN-Ph | 153-156 |
| B-18 | | MeN-cyclohexyl | 172-174 |
| B-19 | | EtN-Ph | 167-169 |
| B-20 | | EtN-CH₂-Ph | 144-146 |
| B-21 | | MeN-(2-MePh) | 179-181 |
| B-22 | | MeN-(3-MePh) | 190-191 |
| B-23 | | MeN-(4-MePh) | 163-165 |
| B-24 | | EtN-(3-MePh) | 145-147 |
| B-25 | | EtN-(2,3-diMePh) | 83-90 |
| B-26 | | MeN-(2,5-diMePh) | 182-184 |
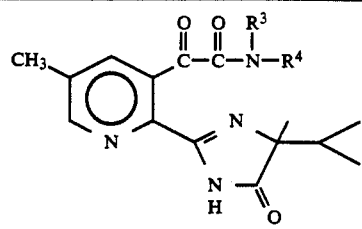
| Compd. No. | K No. | R³—N—R⁴ | m.p. (°C.) |
|---|---|---|---|
| B-27 | | MeN-(3,4-diMePh) | 192-193 |
| B-28 | | EtN-(2,5-diMePh) | 159-160 |
| B-29 | | MeN-(2-OMePh) | 181-183 |
| B-30 | | MeN-(3-OMePh) | 183-184 |
| B-31 | | MeN-(4-OC(O)CH₃Ph) | 179-181 |
| B-32 | | EtN-(4-OMePh) | 191-192 |
| B-33 | | MeN-(4-EtPh) | 155-157 |
| B-34 | | MeN-(4-iPrPh) | 134-138 |
| B-35 | | MeN-(4-OiPrPh) | 142-144 |
| B-36 | | MeN-(4-n-BuPh) | Amorphus Solid |

TABLE 2-continued
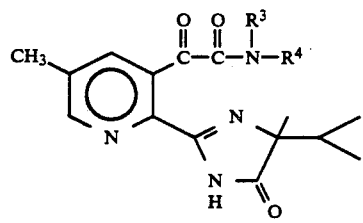
| Compd. No. | K No. | $R^3-N-R^4$ | m.p. (°C.) |
|---|---|---|---|
| B-37 | | Me-N-C6H4-t-Bu | 188–189 |
| B-38 | | Me-N-(2-OCH3,5-CH3-C6H3) | 154–157 |
| B-39 | | N-(2,3-dihydroindol-1-yl)ethyl | 134–136 |
| B-40 | | MeN-(2-Cl-C6H4) | 171–172 |
| B-41 | | Me-N-(3-Cl-C6H4) | 181–183 |
| B-42 | | Me-N-(4-Cl-C6H4) | 145–149 |
| B-43 | | Me-N-(4-Br-C6H4) | 165–167 |
| B-44 | | Et-N-(4-Cl-C6H4) | 162–163 |
| B-45 | | MeN-(3-Cl,4-OMe-C6H3) | 187–189 |
| B-46 | | MeN-(3-Cl,4-CH3-C6H3) | 180–182 |
TABLE 2-continued
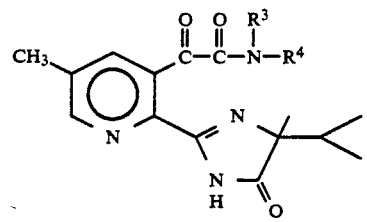
| Compd. No. | K No. | $R^3-N-R^4$ | m.p. (°C.) |
|---|---|---|---|
| B-47 | | MeN-(3,4-Cl2-C6H3) | 200–201 |
| B-48 | | MeN-(3-Cl,4-F-C6H3) | 212–215 |
| B-49 | | MeN-(2-Cl,4-CF3-C6H3) | 182–184 |
| B-50 | | Me-N-(2-F,4-Cl,5-OMe-C6H2) | 167–169 |
| B-51 | | EtN-(4-CH3,3-F-C6H3) | 168–170 |
| B-52 | | EtN-(2-F-C6H4) | 155–157 |
| B-53 | | EtN-(4-F-C6H4) | 155–157 |
| B-54 | | MeN-(3-F-C6H4) | 169–171 |
| B-55 | | MeN-(4-F-C6H4) | 169–171 |

TABLE 2-continued

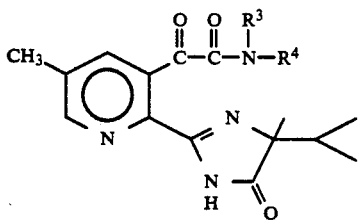

| Compd. No. | K No. | R³—N—R⁴ | m.p. (°C.) |
|---|---|---|---|
| B-56 | | 2-F-C₆H₄-N(Me)- | 158-160 |
| B-57 | | 2,4-F₂-C₆H₃-N(Me)- | 175-177 |
| B-58 | | 2,5-F₂-C₆H₃-N(Me)- | 174-176 |
| B-59 | | 3,4-F₂-C₆H₃-N(Me)- | 173-175 |
| B-60 | | 3-CF₃-C₆H₄-N(Me)- | 178-180 |
| B-61 | | 2-CF₃-4-Cl-C₆H₃-N(Me)- | 167-169 |
| B-62 | | 3,4-(OMe)₂-C₆H₃-N(Et)- | 170-171 |
| B-63 | | 3,4-(OCH₂O)-C₆H₃-N(Et)- | 159-162 |
| B-64 | | 3-SMe-C₆H₄-N(Me)- | 172-175 |
| B-65 | | 3-S(O)Me-C₆H₄-N(Me)- | 164-167 |
| B-66 | | 3-SO₂Me-C₆H₄-N(Me)- | 187-189 |
| B-67 | | 4-NMe₂-C₆H₄-N(Me)- | 187-189 |
| B-68 | | NHCH₃ | 174-178 |
| B-69 | | NH-n-Pr | Amorphus Solid |
| B-70 | | NH-t-Bu | Amorphus Solid |
| B-71 | | NH-CH₂CH₂Cl | 189-191 |
| B-72 | | MeN-CH₂CH₃ | 142-144 |
| B-73 | | 2-pyridyl-N-CH₂CH₃ | 143-145 |
| B-74 | | 4-(tetrahydrothiopyranyl)-C₆H₄-N(Me)- | 167-168 |
| B-75 | | 4-PhO-C₆H₄-N(Me)- | 107-112 |
| B-76 | | 4-SMe-C₆H₄-N(Me)- | 145-148 |

TABLE 2-continued

Structure: 5-methylpyridine with C(=O)C(=O)N(R³)R⁴ at 3-position and imidazolinone substituent at 2-position (with t-butyl and NH, C=O)

| Compd. No. | K No. | R³—N—R⁴ | m.p. (°C.) |
|---|---|---|---|
| B-77 | | 2,2-dimethyl-2,3-dihydrobenzofuran-7-yl(methyl)amino (MeN-) | 168–169 |
| B-78 | | 3-chloro-4-(trifluoromethyl)phenyl(ethyl)amino (EtN-, Cl, CF₃) | 159–161 |
| B-79 | | MeN-CH₂-OMe (methoxymethyl(methyl)amino) | 159–161 |
| B-80 | | MeN—C₆H₄—CF₃ (4-(trifluoromethyl)phenyl(methyl)amino) | — |
| B-81 | | MeN—C₆H₃(F)(CH₃) (3-fluoro-4-methylphenyl(methyl)amino) | — |

TABLE 3

Structure: 5-ethylpyridine with C(=O)C(=O)N(R³)R⁴ at 3-position and imidazolinone substituent at 2-position (with t-butyl and NH, C=O)

| Compd. No. | K No. | R³—N—R⁴ | m.p. (°C.) |
|---|---|---|---|
| C-1 | | MeNMe | 148–150 |
| C-2 | | EtNEt | 135–138 |
| C-3 | | N—Pr—N—Pr | 114–116 |
| C-4 | | piperidine | 149–150 |
| C-5 | | morpholine | 169–171 |
| C-6 | | 1,2,3,6-tetrahydropyridine | 161–165 |
| C-7 | | hexamethyleneimine (azepane) | 154–156 |
| C-8 | | 4-methylpiperazine | Amorphus Solid |
| C-9 | | diallylamine | 216–218 |
| C-10 | | MeN-CH₂-C≡CH (N-methylpropargylamine) | 139–141 |
| C-11 | | 2,5-dihydro-1H-pyrrole | 185–187 |
| C-12 | | MeN—Ph | 131–134 |
| C-13 | | MeN—(tetrahydrothiopyran-4-yl) | 179–181 |
| C-14 | | Et—N—(2-pyridyl) | 134–136 |
| C-15 | | EtNCH₂—Ph | 149–151 |
| C-16 | | n-BuN—CH₂—Ph | Amorphus Solid |
| C-17 | | EtN—(3-methylphenyl) | 118–120 |

TABLE 3-continued

[Structure: 5-Et-pyridine with 2-(4-tert-butyl-5-oxo-imidazolin-2-yl) and 3-C(O)C(O)N(R³)R⁴ substituents]

| Compd. No. | K No. | R³—N—R⁴ | m.p. (°C.) |
|---|---|---|---|
| C-18 | | MeN-C₆H₄-OMe (o-OMe) | 152–154 |
| C-19 | | MeN-C₆H₄-t-Bu (p-t-Bu) | Amorphus Solid |
| C-20 | | MeN-C₆H₄-Cl (o-Cl) | 155–157 |
| C-21 | | Me-N-C₆H₃(Cl)(OMe) | 163–165 |
| C-22 | | MeN-C₆H₃(F)(CH₃) | 136–138 |
| C-23 | | MeN-C₆H₃(Cl)(F) | 177–179 |
| C-24 | | EtN-C₆H₄-F | 140–142 |
| C-25 | | Me-N-C₆H₄-F (m-F) | 133–135 |
| C-26 | | Me-N-C₆H₃(F)(F) (2,4-F₂) | 155–158 |
| C-27 | | Me-N-C₆H₃(F)(F) (2,5-F₂) | 152–154 |
| C-28 | | MeN-C₆H₄-CF₃ | 131–133 |
| C-29 | | Me-N-C₆H₃(Cl)(Me)(CF₃) | 181–183 |
| C-30 | | NH-iPr | 88–90 |
| C-31 | | NH-CH₂CH₂Cl | 181–184 |
| C-32 | | NH—Et | 177–178 |
| C-33 | | (t-Bu)N-CH₂CH₂OH | 53–56 |
| C-34 | | NH₂ | 197–203 |

TABLE 4

[Structure: Quinoline with 2-(4-tert-butyl-5-oxo-imidazolin-2-yl) and 3-C(O)C(O)N(R³)R⁴ substituents]

| Compd. No. | K No. | R³—N—R⁴ | m.p. (°C.) |
|---|---|---|---|
| D-1 | | Me—N—Me | 178–180 |
| D-2 | | piperidinyl | 150–154 |

TABLE 4-continued

[Structure: quinoline system with C(=O)-C(=O)-N(R³)(R⁴) at position 3, and a =N-C(C(CH₃)₃)-C(=O)-NH ring at position 2]

| Compd. No. | K No. | R³—N—R⁴ | m.p. (°C.) |
|---|---|---|---|
| D-3 | | [tetrahydropyridine ring with N] | 177–179 |
| D-4 | | [piperazine ring with N—CH₃] | 189–191 |
| D-5 | | CH₂=CH-CH₂-N-CH₂-CH=CH₂ (diallylamine) | 169–171 |
| D-6 | | Me—N—phenyl | 163–166 |

EXAMPLE 4

Post-emergence herbicidal evaluation of test compounds

The post-emergence herbicidal activity of the compounds of the invention is demonstrated by the following tests, wherein a variety of monocotyledonous and dicotyledonous plants are treated with test compounds dispersed in aqueous acetone mixtures. In the tests, seedling plants are grown in jiffy flats for two weeks. The test compounds are dispersed in 50/50 acetone/water mixtures containing 0.5% TWEEN(TM) 20, a polyoxyethylene sorbitan monolaurate surfactant, in sufficient quantity to provide the equivalent of about 0.06 kg of 10 kg per hectare of active compound when applied to the plants through a spray nozzle operating at 40 psi for a predetermined time. After spraying, the plants are placed on greenhouse benches and are cared for in the usual manner, commensurate with conventional greenhouse practices.

From 2 to 4 weeks after treatment, the seedling plants, are examined and rated according to the rating system provied below.

The data obtained are recorded in table 6 below.

[Rating System]

| Rating System | % Difference in Growth |
|---|---|
| No effect | 0 |
| Possible effect | 1~10 |
| Slight effect | 1~25 |
| Moderate effect | 26~40 |
| Definite injury | 41~60 |
| Herbicidal effect | 61~75 |
| Good herbicidal effect | 76~90 |
| Approaching complete kill | 91~99 |
| Complete kill | 100 |

In most cases the data are a single test, but in several instances, they are average values obtained from more than one test.

TABLE 5

Test to evaluate herbicidal activity

| Abbr. | Scientific Name | Plants applied |
|---|---|---|
| (Testgroup I: UPLAND SPECIES) | | |
| LYPES | Lycopersicon esculentum MILL. | Tomato |
| TRZAW | Triticum aestivum L. | Wheat |
| GLXMX | Glycine max(L.) MERR. | Soybean |
| ZEAMX | Zea mays L. | Corn |
| DACGL | Dactylis glomerata L. | Orchardgrass |
| AMAVI | Amaranthus viridis L. | Pigweed |
| DIGSA | Digitaria sanguinalis(L.) SCOP. | Large crabgrass |
| RUMJA | Rumex japonicus HOUTT. | Dock |
| AESIN | Aeschynomene indica L. | Indian jointvetch |
| CAGHE | Calystegia japonica CHOISY | Bindweed |
| POLHY | Polygonum hydropiper L. | Smartweed |
| (Test group II: PADDY SPECIES) | | |
| ORYSA | Oryza sativa L. | Rice |
| ECHOR | Echinochloa crus-galli P. Beauv. var. oryzicola OHWI | Barnyardgrass |
| CYPDI | Cyperus difformis L. | Umbrellaplant |
| ANEKE | Aneilema keisak HASSK | Dayflower |

EXAMPLE 5

Pre-emergence herbicidal evaluation of test compounds

The pre-emergence herbicidal activity of the compounds of the invention is examplified by the following tests in which the seeds of a variety of monocotyledonos and dicotyledonous plants are seperated mixed with potting soil in separated pint cups. After planting, the cups are sprayed with the selected aqueous acetone solution containing test compound in sufficient quantity to provide the equivalent of about 0.06 to 10 kg per hectare of test compound per cup. The treated cups are then placed on greenhouse benches, watered and cared for in accordance with conventional greenhouse procedures. From 2 to 4 weeks after treatment, the tests are terminated and each cup is examined and rated according to the rating system set forth above. The herbicidal proficiency of the active ingredients of the present invention is evident from the test results which are recorded in Table 6 below.

Table 6 below is represented pre-and post-emerergence herbicidal evaluation [PRIMARY SCREENING (Herbicide)]of test compounds.

TABLE 6

PRIMARY SCREENING (Herbicide)

| KSC CHEM. NO. REF. | TYPE | kg/ha | UPLAND WEED SPECIES ||||||||||||| PADDY WEED SPECIES ||||
|---|---|---|---|---|---|---|---|---|---|---|---|---|---|---|---|---|---|---|
| | | | LYPES | TRZAW | GLXMX | ZEAMX | DACGL | AMAVI | DIGSA | RUMJA | POLHY | AESIN | CAGHE | URYSA | ECHOR | CYPDI | ANEXE |
| (A-1) | PRE | .25 | 100 | 100 | 90 | 90 | 70 | 100 | 100 | 80 | 100 | 100 | 100 | 60 | 70 | 70 | 70 |
| | | .125 | 100 | 100 | 70 | 50 | 70 | 100 | 90 | 70 | 90 | 90 | 100 | 60 | 20 | 60 | 10 |
| | | .06 | 100 | 90 | 40 | 10 | 35 | 100 | 90 | 10 | 90 | 70 | 90 | 0 | 0 | 50 | 10 |
| | | .03 | 90 | 50 | 0 | 0 | 10 | 60 | 60 | 0 | 70 | 0 | 80 | 0 | 0 | 0 | 0 |
| | | .015 | 90 | 10 | 0 | 0 | 0 | 0 | 20 | 0 | 0 | 0 | 10 | 0 | 0 | 0 | 0 |
| | POST | .5 | 100 | 100 | 95 | 100 | 100 | 100 | 100 | 90 | 90 | 80 | 100 | 90 | 90 | 100 | 55 |
| | | .25 | 100 | 100 | 90 | 90 | 80 | 100 | 100 | 80 | 80 | 70 | 100 | 90 | 80 | 100 | 50 |
| | | .125 | 100 | 100 | 65 | 65 | 65 | 100 | 80 | 60 | 80 | 35 | 90 | 70 | 55 | 100 | 20 |
| | | .06 | 80 | 90 | 0 | 0 | 55 | 70 | 55 | 40 | 70 | 35 | 50 | 15 | 20 | 40 | 20 |
| | | .03 | 70 | 55 | 10 | 0 | 10 | 50 | 10 | 0 | 70 | 10 | 40 | 15 | 15 | 0 | 0 |
| (A-2) | PRE | .25 | 100 | 60 | 70 | 70 | 70 | 80 | 90 | 20 | 70 | 50 | 80 | 60 | 35 | 90 | 25 |
| | POST | .25 | 100 | 90 | 70 | 70 | 70 | 100 | 100 | 60 | 70 | 70 | 100 | 70 | 80 | 60 | 30 |
| (A-3) | PRE | .25 | 100 | 90 | 60 | 60 | 65 | 90 | 80 | 40 | 95 | 50 | 65 | 70 | 20 | 90 | 70 |
| | POST | .25 | 90 | 85 | 30 | 65 | 70 | 80 | 100 | 65 | 90 | 75 | 80 | 90 | 70 | 50 | 70 |
| (A-4) | PRE | .25 | 90 | 70 | 15 | 60 | 65 | 90 | 80 | 20 | 70 | 70 | 90 | 70 | 70 | 60 | 40 |
| | POST | .25 | 100 | 90 | 85 | 100 | 80 | 100 | 100 | 70 | 80 | 90 | 100 | 90 | 90 | 80 | 70 |
| (A-5) | PRE | .25 | 90 | 80 | 10 | 40 | 70 | 90 | 100 | 40 | 80 | 70 | 90 | 100 | 70 | 90 | 70 |
| | POST | .25 | 100 | 100 | 85 | 100 | 100 | 100 | 100 | 95 | 100 | 70 | 100 | 90 | 90 | 70 | 45 |
| (A-6) | PRE | .25 | 100 | 90 | 70 | 80 | 70 | 90 | 90 | 70 | 85 | 95 | 95 | 90 | 90 | 100 | 100 |
| | POST | .25 | 100 | 100 | 90 | 100 | 100 | 100 | 100 | 70 | 100 | 70 | 100 | 100 | 100 | 100 | 70 |
| (A-7) | PRE | .25 | 100 | 85 | 35 | 20 | 70 | 100 | 90 | 80 | 70 | 90 | 65 | 65 | 20 | 50 | 90 |
| | POST | .25 | 90 | 70 | 80 | 100 | 70 | 100 | 90 | 50 | 80 | 60 | 80 | 90 | 10 | 70 | 15 |
| (A-8) | PRE | .25 | 70 | 30 | 0 | 20 | 60 | 80 | 70 | 50 | 75 | 0 | 0 | 55 | 55 | 40 | 10 |
| | POST | .25 | 40 | 10 | 0 | 0 | 60 | 80 | 60 | 55 | 95 | 25 | 40 | 70 | 20 | 60 | 50 |
| (A-9) | PRE | .25 | 100 | 100 | 70 | 80 | 100 | 100 | 100 | 90 | 100 | 100 | 100 | 20 | 20 | 80 | 25 |
| (A-10) | POST | .25 | 100 | 100 | 100 | 100 | 70 | 100 | 70 | 85 | 90 | 90 | 100 | 100 | 100 | 65 | 40 |
| | PRE | .25 | 100 | 100 | 100 | 100 | 90 | 100 | 100 | 85 | 90 | 90 | 100 | 100 | 40 | 70 | BE 90 |
| (A-11) | POST | .25 | 90 | 70 | 20 | 20 | 80 | 70 | 90 | 100 | 100 | 100 | 50 | 15 | 100 | 100 | 0 |
| | PRE | .25 | 100 | 100 | 30 | 30 | 25 | 100 | 30 | 10 | 35 | 35 | 70 | 90 | 0 | 70 | 100 |
| (A-12) | POST | .25 | 70 | 95 | 65 | 100 | 90 | 100 | 100 | 90 | 95 | 100 | 100 | 85 | 65 | 0 | 0 |
| | PRE | .25 | 100 | 100 | 90 | 100 | 100 | 100 | 100 | 100 | 100 | 90 | 100 | 100 | 90 | 95 | 65 |
| (A-13) | POST | .25 | 70 | 70 | 20 | 20 | 0 | 60 | 70 | 10 | 95 | 50 | 70 | 15 | 10 | 70 | 90 |
| | PRE | .25 | 100 | 90 | 100 | 100 | 80 | 100 | 25 | 90 | 70 | 70 | 70 | 65 | 70 | 90 | 90 |
| (A-14) | POST | .25 | 90 | 80 | 0 | 0 | 75 | 100 | 100 | 60 | 100 | 75 | 90 | 60 | 100 | 75 | 0 |
| | PRE | .25 | 80 | 70 | 80 | 90 | 30 | 70 | 65 | 10 | 90 | 0 | 30 | 55 | 10 | 65 | 90 |
| (A-15) | POST | .25 | 90 | 100 | 20 | 0 | 100 | 100 | 35 | 10 | | 60 | 100 | 80 | 65 | 65 | 25 |
| | PRE | .25 | 70 | 70 | 75 | 70 | 20 | 100 | 60 | 10 | | 15 | 30 | 60 | 60 | 55 | 30 |
| (A-16) | POST | .25 | 100 | 100 | 30 | 0 | 100 | 100 | 70 | 10 | | 65 | 100 | 10 | 20 | 0 | 60 |
| | PRE | .25 | 35 | 35 | 65 | 70 | 20 | 60 | 35 | 15 | 70 | 0 | 30 | 70 | 70 | 20 | 0 |
| (A-17) | POST | .25 | 70 | 70 | 10 | 0 | 10 | 100 | 60 | 10 | | 40 | 50 | 10 | 25 | 90 | 30 |
| | PRE | .25 | 90 | 90 | 55 | 100 | 85 | 60 | 35 | 90 | 70 | 80 | 85 | 50 | 100 | 100 | 30 |
| (A-18) | POST | .25 | 100 | 70 | 80 | 0 | 90 | 100 | 100 | 55 | 100 | 85 | 90 | 70 | 10 | 0 | 60 |
| | PRE | .25 | 85 | 90 | 15 | 10 | 20 | 80 | 80 | 10 | 60 | 0 | 40 | 0 | 55 | 20 | 15 |
| (A-19) | POST | .25 | 90 | 100 | 10 | 0 | 10 | 100 | 0 | 0 | 50 | 90 | 60 | 65 | 50 | 90 | 20 |
| | PRE | .25 | 100 | 100 | 80 | 90 | 100 | 100 | 100 | 100 | 100 | 90 | 100 | 80 | 100 | 100 | 70 |
| (A-20) | POST | .25 | 100 | 100 | 70 | 40 | 100 | 100 | 100 | 85 | 100 | 90 | 100 | 100 | 100 | 100 | 60 |

TABLE 6-continued

PRIMARY SCREENING (Herbicide)

| KSC CHEM. NO. REF. | TYPE | kg/ha | UPLAND WEED SPECIES | | | | | | | | | | | | | | PADDY WEED SPECIES | | | |
|---|---|---|---|---|---|---|---|---|---|---|---|---|---|---|---|---|---|---|---|---|
| | | | LYPES | TRZAW | GLXMX | ZEAMX | DACGL | AMAVI | DIGSA | RUMJA | POLHY | AESIN | CAGHE | URYSA | ECHOR | CYPDI | ANEXE |
| (A-21) | PRE | .25 | 90 | 70 | 65 | 55 | 60 | 90 | 100 | 90 | | 50 | 90 | 30 | 10 | 20 | 10 |
| | POST | .25 | 100 | 100 | 80 | 70 | 70 | 100 | 60 | 60 | | 80 | 100 | 100 | 60 | 70 | 70 |
| (A-22) | PRE | .25 | 100 | 90 | 60 | 80 | 100 | 90 | 100 | 80 | 90 | 70 | 80 | 100 | 0 | 80 | 80 |
| | | .125 | 80 | 60 | 40 | 60 | 80 | 90 | 100 | 80 | | | 70 | 100 | 0 | 70 | 60 |
| | | .06 | 80 | 50 | 30 | 50 | 80 | 80 | 100 | 80 | | | 65 | 100 | 0 | 70 | 30 |
| | | .03 | 70 | 40 | 30 | 30 | 70 | 80 | 100 | 50 | | | 40 | 100 | 100 | 70 | 0 |
| | POST | .25 | 100 | 90 | 70 | 65 | 65 | 100 | 100 | 50 | | 75 | 80 | 80 | 70 | 70 | 90 |
| | | .125 | 95 | 55 | 50 | 10 | 20 | 80 | 50 | 30 | | 60 | 65 | 80 | 30 | 65 | 75 |
| | | .06 | 50 | 10 | 20 | 0 | 20 | 60 | 10 | 20 | | 10 | 50 | 65 | 0 | 60 | 50 |
| | | .03 | 50 | 0 | 0 | 0 | 10 | 30 | 50 | 10 | | 0 | 50 | 35 | 20 | 40 | 20 |
| (A-23) | PRE | .25 | 100 | 100 | 75 | 90 | 90 | 100 | 100 | 60 | | 100 | 100 | 70 | 100 | 65 | 65 |
| (A-24) | POST | .25 | 100 | 100 | 80 | 65 | 70 | 100 | 100 | 20 | 85 | 90 | 100 | 50 | 20 | 100 | 60 |
| (A-25) | PRE | .25 | 100 | 100 | 85 | 90 | 100 | 100 | 100 | 80 | 75 | 95 | 90 | 70 | 30 | 65 | 70 |
| | POST | .25 | 100 | 90 | 90 | 70 | 65 | 90 | 80 | 15 | 95 | 80 | 95 | 70 | 50 | 90 | 60 |
| (A-26) | PRE | .25 | 85 | 35 | 0 | 0 | 80 | 80 | 100 | 60 | 90 | 0 | 80 | 60 | 15 | 65 | 0 |
| | POST | .25 | 90 | 15 | 15 | 10 | 30 | 100 | 90 | 35 | 100 | 20 | 90 | 90 | 100 | 100 | 100 |
| (A-27) | PRE | .25 | 90 | 55 | 20 | 10 | 55 | 70 | 60 | 40 | | 30 | 70 | 65 | 10 | 20 | 20 |
| | POST | .25 | 100 | 60 | 80 | 10 | 40 | 100 | 15 | 20 | | 20 | 60 | 20 | 30 | 0 | 15 |
| (A-28) | PRE | .25 | 100 | 95 | 80 | 100 | 90 | 100 | 100 | 95 | 85 | 95 | 95 | 70 | 50 | 80 | 75 |
| | POST | .25 | 100 | 100 | 100 | 100 | 65 | 100 | 80 | 70 | 75 | 90 | 100 | 70 | 30 | 40 | 95 |
| (A-29) | PRE | .25 | 100 | 90 | 85 | 90 | 80 | 100 | 100 | 80 | 95 | 90 | 100 | 70 | 50 | 70 | 90 |
| | POST | .25 | 100 | 90 | 80 | 90 | 75 | 100 | 100 | 70 | 90 | 90 | 100 | 60 | 30 | 60 | 40 |
| | | .125 | 100 | 70 | 80 | 50 | 80 | 100 | 100 | 90 | 100 | 50 | 80 | 90 | 40 | 80 | 100 |
| | | .06 | 90 | 60 | 40 | 20 | 80 | 80 | 100 | 80 | | 10 | 80 | 100 | 0 | 70 | 0 |
| | | .03 | 80 | 40 | 20 | 0 | 65 | 70 | 70 | 80 | | 0 | 50 | 100 | 0 | 60 | 0 |
| | POST | .25 | 70 | 95 | 65 | 0 | 100 | 100 | 100 | 100 | | 90 | 100 | 100 | 0 | 60 | 0 |
| (A-30) | PRE | .25 | 90 | 90 | 45 | 0 | 60 | 80 | 95 | 30 | | 70 | 85 | 90 | 95 | 100 | 90 |
| | POST | .25 | 100 | 70 | 10 | 0 | 0 | 100 | 40 | 10 | 30 | 0 | 80 | 85 | 75 | 80 | 85 |
| (A-31) | PRE | .25 | 70 | 20 | 10 | 0 | 0 | 80 | 0 | 0 | | 0 | 55 | 70 | 40 | 50 | 70 |
| | POST | .25 | 100 | 40 | 70 | 30 | 70 | 65 | 65 | 30 | | 0 | 30 | 10 | 20 | 50 | 10 |
| (A-32) | PRE | .25 | 100 | 90 | 80 | 90 | 90 | 100 | 100 | 70 | 100 | 85 | 100 | 60 | 60 | 70 | 90 |
| | POST | .25 | 100 | 100 | 90 | 55 | 90 | 100 | 70 | 30 | | 100 | 100 | 80 | 35 | 80 | 70 |
| (A-33) | PRE | .25 | 100 | 90 | 85 | 90 | 80 | 100 | 70 | 50 | | 90 | 95 | 90 | 100 | 100 | 60 |
| | POST | .25 | 100 | 100 | 65 | 100 | 85 | 100 | 100 | 70 | 80 | 100 | 100 | 65 | 20 | 100 | 20 |
| (A-34) | PRE | .25 | 90 | 90 | 80 | 85 | 100 | 100 | 100 | 25 | | 80 | 90 | 35 | 10 | 70 | 100 |
| | POST | .25 | 100 | 65 | 50 | 40 | 60 | 100 | 70 | 15 | 65 | 90 | 100 | 90 | 10 | 100 | 0 |
| (A-35) | PRE | .25 | 90 | 70 | 60 | 10 | 60 | 100 | 70 | 25 | | 40 | 90 | 30 | 60 | 80 | 80 |
| | POST | .25 | 80 | 100 | 15 | 5 | 40 | 80 | 25 | 30 | 90 | 60 | 70 | 60 | 0 | 30 | 0 |
| (A-36) | PRE | .25 | 100 | 65 | 80 | 15 | 50 | 100 | 70 | 40 | | 40 | 70 | 0 | 50 | 50 | 50 |
| | POST | .25 | 70 | 100 | 20 | 10 | 35 | 80 | 60 | 20 | 70 | 50 | 80 | 80 | 30 | 30 | 10 |
| (A-37) | PRE | .25 | 90 | 35 | 50 | 10 | 25 | 100 | 30 | 10 | 65 | 15 | 30 | 30 | 20 | 10 | 0 |
| | POST | .25 | 80 | 60 | 5 | 10 | 20 | 80 | 15 | 0 | 75 | 20 | 70 | 0 | 20 | 0 | 0 |
| (A-38) | PRE | .25 | 100 | 100 | 50 | 0 | 20 | 100 | 15 | 10 | | 0 | 80 | 10 | 60 | 0 | 0 |
| | POST | .25 | 100 | 100 | 70 | 70 | 90 | 100 | 100 | 90 | 90 | 75 | 90 | 60 | 30 | 20 | 0 |
| (A-39) | PRE | .25 | 90 | 100 | 90 | 75 | 80 | 100 | 100 | 70 | | 80 | 70 | 100 | 100 | 100 | 90 |

TABLE 6-continued
PRIMARY SCREENING (Herbicide)

| KSC CHEM. NO. REF. | TYPE | kg/ha | UPLAND WEED SPECIES | | | | | | | | | | | | | | PADDY WEED SPECIES | | | |
|---|---|---|---|---|---|---|---|---|---|---|---|---|---|---|---|---|---|---|---|---|
| | | | LYPES | TRZAW | GLXMX | ZEAMX | DACGL | AMAVI | DIGSA | RUMJA | POLHY | AESIN | CAGHE | URYSA | ECHOR | CYPDI | ANEXE |
| (B-1) | POST | .25 | 70 | 60 | 40 | 10 | 20 | 100 | 30 | 10 | 80 | 10 | 70 | 10 | 0 | 0 | 20 |
| | PRE | .5 | 100 | 30 | 0 | 0 | 60 | 70 | 100 | 55 | 80 | 20 | 80 | 70 | 70 | 90 | 90 |
| | | .25 | 80 | 0 | 0 | 0 | 40 | 60 | 70 | 30 | 30 | 0 | 80 | 40 | 50 | 70 | 10 |
| | | .125 | 70 | 0 | 0 | 0 | 0 | 0 | 65 | 0 | 10 | 0 | 10 | 0 | 0 | 60 | 0 |
| | | .06 | 70 | 0 | 0 | 0 | 0 | 0 | 10 | 0 | 0 | 0 | 0 | 0 | 0 | 70 | 0 |
| | POST | .5 | 90 | 40 | 5 | 0 | 80 | 70 | 90 | 10 | 80 | 55 | 60 | 70 | 60 | 60 | 30 |
| | | .25 | 80 | 5 | 0 | 0 | 60 | 50 | 65 | 0 | 50 | 10 | 40 | 50 | 15 | 50 | 10 |
| | | .125 | 70 | 0 | 0 | 0 | 10 | 20 | 20 | 10 | 10 | 0 | 10 | 50 | 0 | 20 | 0 |
| | | .06 | 40 | 0 | 0 | 0 | 0 | 0 | 0 | 0 | 0 | 0 | 0 | 20 | 0 | 0 | 0 |
| (B-2) | PRE | .5 | 100 | 90 | 90 | 90 | 90 | 90 | 100 | 90 | 90 | 90 | 90 | 100 | 90 | 100 | 90 |
| | | .25 | 100 | 90 | 65 | 70 | 70 | 90 | 100 | 90 | 90 | 90 | 90 | 100 | 90 | 100 | 80 |
| | | .125 | 100 | 85 | 10 | 30 | 70 | 90 | 100 | 80 | 90 | 80 | 90 | 90 | 80 | 90 | 70 |
| | | .06 | 90 | 70 | 0 | 0 | 60 | 90 | 100 | 80 | 90 | 65 | 100 | 80 | 100 | 90 | 60 |
| | POST | .5 | 100 | 90 | 75 | 90 | 90 | 90 | 100 | 90 | 90 | 95 | 100 | 100 | 100 | 100 | 95 |
| | | .25 | 100 | 90 | 65 | 85 | 85 | 90 | 100 | 80 | 80 | 70 | 90 | 100 | 70 | 90 | 90 |
| | | .125 | 100 | 85 | 30 | 35 | 70 | 90 | 100 | 80 | 90 | 70 | 50 | 100 | 80 | 100 | 80 |
| | | .06 | 95 | 65 | 10 | 0 | 60 | 80 | 90 | 80 | 80 | 35 | 90 | 70 | 90 | 90 | 50 |
| | | .03 | 90 | 10 | 0 | 0 | 60 | 80 | 90 | 40 | 70 | 0 | 65 | 60 | 30 | 55 | 0 |
| (B-3) | POST | .5 | 100 | 90 | 85 | 80 | 90 | 90 | 100 | 70 | 90 | 100 | 100 | 90 | 100 | 100 | 50 |
| | | .25 | 100 | 90 | 65 | 80 | 80 | 90 | 100 | 70 | 90 | 70 | 90 | 80 | 100 | 100 | 50 |
| | | .125 | 100 | 80 | 40 | 65 | 70 | 90 | 100 | 70 | 90 | 60 | 100 | 70 | 90 | 100 | 40 |
| | PRE | .25 | 100 | 50 | 15 | 10 | 65 | 70 | 90 | 50 | 80 | 60 | 60 | 90 | 75 | 100 | 40 |
| (B-4) | POST | .25 | 90 | 60 | 10 | 55 | 70 | 70 | 100 | 70 | 90 | 30 | 90 | 80 | 80 | 90 | 60 |
| | PRE | .25 | 100 | 65 | 10 | 30 | 65 | 90 | 100 | 70 | 80 | 60 | 65 | 80 | 100 | 70 | 45 |
| (B-5) | POST | .25 | 100 | 50 | 10 | 20 | 50 | 90 | 100 | 55 | 70 | 10 | 80 | 70 | 70 | 90 | 70 |
| | PRE | .25 | 100 | 65 | 10 | 40 | 70 | 90 | 100 | 35 | 70 | 25 | 50 | 100 | 80 | 70 | 30 |
| (B-6) | POST | .25 | 80 | 60 | 40 | 15 | 60 | 100 | 80 | 40 | 80 | 0 | 80 | 70 | 90 | 90 | 80 |
| | PRE | .25 | 100 | 65 | 50 | 30 | 60 | 80 | 100 | 70 | 80 | 50 | 60 | 90 | 90 | 90 | 35 |
| (B-7) | POST | .25 | 100 | 80 | 25 | 65 | 90 | 90 | 90 | 100 | 90 | 50 | 100 | 90 | 90 | 90 | 60 |
| | PRE | .25 | 90 | 80 | 60 | 30 | 90 | 90 | 100 | 70 | 90 | 80 | 90 | 100 | 95 | 90 | 50 |
| (B-8) | POST | .25 | 100 | 90 | 80 | 80 | 80 | 90 | 100 | 70 | 90 | 50 | 90 | 90 | 95 | 90 | 60 |
| | PRE | .25 | 100 | 70 | 40 | 65 | 70 | 80 | 100 | 60 | 80 | 60 | 100 | 90 | 90 | 90 | 50 |
| (B-9) | POST | .25 | 100 | 90 | 80 | 70 | 90 | 90 | 100 | 70 | 90 | 85 | 100 | 100 | 100 | 90 | 90 |
| | PRE | .25 | 90 | 70 | 0 | 70 | 80 | 90 | 100 | 70 | 80 | 65 | 60 | 90 | 95 | 90 | 60 |
| (B-10) | POST | .25 | 100 | 65 | 65 | 60 | 80 | 100 | 100 | 70 | 80 | 80 | 80 | 100 | 100 | 90 | 85 |
| | PRE | .25 | 90 | 40 | 10 | 30 | 65 | 80 | 95 | 90 | 90 | 40 | 70 | 90 | 60 | 95 | 70 |
| (B-11) | POST | .25 | 100 | 70 | 25 | 30 | 70 | 100 | 100 | 80 | 100 | 65 | 90 | 90 | 85 | 90 | 60 |
| | PRE | .25 | 100 | 80 | 50 | 30 | 80 | 100 | 100 | 80 | 80 | 50 | 70 | 90 | 20 | 90 | 30 |
| (B-12) | POST | .25 | 100 | 90 | 55 | 60 | 70 | 100 | 100 | 90 | 90 | 80 | 90 | 90 | 100 | 90 | 60 |
| | PRE | .25 | 100 | 65 | 10 | 10 | 80 | 95 | 100 | 90 | 80 | 70 | 80 | 100 | 95 | 90 | 70 |
| (B-13) | POST | .25 | 100 | 60 | 40 | 45 | 100 | 80 | 95 | 40 | 100 | 60 | 80 | 90 | 100 | 100 | 10 |
| | PRE | .25 | 100 | 70 | 65 | 75 | 90 | 100 | 100 | 50 | 80 | 65 | 95 | 100 | 70 | 70 | 65 |
| (B-14) | POST | .25 | 90 | 60 | 30 | 70 | 70 | 80 | 100 | 70 | 100 | 90 | 100 | 90 | 100 | 90 | 50 |
| | PRE | .25 | 100 | 50 | 60 | 60 | 80 | 100 | 100 | 40 | 80 | 60 | 70 | 70 | 70 | 60 | 20 |
| (B-15) | POST | .25 | 100 | 90 | 50 | 80 | 100 | 100 | 100 | 50 | 80 | 65 | 100 | 100 | 100 | 80 | 25 |
| | PRE | .25 | 100 | 75 | 35 | 90 | 100 | 100 | 100 | 95 | 90 | 90 | 100 | 100 | 100 | 95 | 80 |
| (B-16) | POST | .25 | 100 | 30 | 60 | 10 | 90 | 90 | 100 | 70 | 100 | 75 | 100 | 100 | 100 | 100 | 70 |
| | PRE | .25 | 90 | 30 | 10 | 10 | 90 | 90 | 100 | 70 | 90 | 10 | 70 | 100 | 85 | 95 | 35 |

TABLE 6-continued

PRIMARY SCREENING (Herbicide)

| KSC CHEM. NO. REF. | TYPE | kg/ha | UPLAND WEED SPECIES ||||||||||||| PADDY WEED SPECIES ||||
|---|---|---|---|---|---|---|---|---|---|---|---|---|---|---|---|---|---|---|
| | | | LYPES | TRZAW | GLXMX | ZEAMX | DACGL | AMAVI | DIGSA | RUMJA | POLHY | AESIN | CAGHE | URYSA | ECHOR | CYPDI | ANEXE |
| (B-17) | POST | .25 | 100 | 30 | 30 | 10 | 70 | 100 | 70 | 60 | 80 | 40 | 90 | 100 | 100 | 80 | 40 |
| | PRE | .5 | 100 | 90 | 70 | 100 | 95 | 90 | 100 | 90 | 90 | 90 | 100 | 100 | 100 | 100 | 80 |
| | | .25 | 100 | 90 | 50 | 65 | 90 | 90 | 100 | 90 | 90 | 80 | 100 | 100 | 90 | 90 | 90 |
| | | .125 | 100 | 70 | 10 | 20 | 80 | 90 | 100 | 80 | 90 | 70 | 100 | 85 | 70 | 70 | 80 |
| | | .06 | 90 | 30 | 0 | 0 | 70 | 85 | 90 | 70 | 80 | 35 | 90 | 50 | 65 | 70 | 35 |
| | | .03 | 90 | 15 | 0 | 0 | 60 | 70 | 80 | 50 | 70 | 10 | 60 | 30 | 20 | 10 | 10 |
| | POST | .5 | 100 | 100 | 90 | 90 | 100 | 100 | 100 | 90 | 100 | 100 | 100 | 90 | 100 | 100 | 65 |
| | | .25 | 100 | 70 | 15 | 5 | 100 | 100 | 100 | 80 | 85 | 85 | 100 | 70 | 90 | 100 | 65 |
| | | .125 | 90 | 35 | 10 | 0 | 60 | 100 | 100 | 65 | 70 | 55 | 100 | 10 | 80 | 70 | 55 |
| | | .06 | 70 | 10 | 0 | 0 | 25 | 30 | 60 | 10 | 50 | 10 | 55 | 10 | 25 | 20 | 20 |
| | | .03 | 65 | 10 | 0 | 0 | 0 | 20 | 90 | 0 | 40 | 0 | 65 | 0 | 0 | 0 | 0 |
| (B-18) | PRE | .25 | 80 | 50 | 15 | 0 | 70 | 90 | 100 | 85 | | 0 | 70 | 60 | 30 | 20 | 10 |
| (B-19) | POST | .25 | 90 | 10 | 10 | 0 | 70 | 0 | 100 | 80 | 100 | 25 | 65 | 70 | 70 | 70 | 15 |
| (B-20) | PRE | .25 | 100 | 60 | 20 | 25 | 90 | 95 | 100 | 90 | | 30 | 90 | 70 | 60 | 70 | 20 |
| | POST | .25 | 100 | 60 | 10 | 50 | 100 | 100 | 100 | 90 | 100 | 90 | 100 | 100 | 90 | 90 | 40 |
| | PRE | .25 | 80 | 0 | 20 | 20 | 65 | 90 | 95 | 50 | | 0 | 70 | 70 | 70 | 90 | 10 |
| (B-21) | POST | .25 | 100 | 65 | 20 | 0 | 100 | 100 | 100 | 90 | | 70 | 100 | 70 | 80 | 70 | 60 |
| (B-22) | PRE | .25 | 80 | 0 | 20 | 0 | 60 | 70 | 90 | 20 | | 0 | 65 | 50 | 0 | 0 | 20 |
| | PRE | .25 | 100 | 15 | 65 | 65 | 90 | 90 | 100 | 100 | 90 | 25 | 100 | 100 | 80 | 80 | 70 |
| | | .125 | 100 | 80 | 30 | 30 | 90 | 100 | 100 | 70 | | 90 | 100 | 70 | 20 | 90 | 60 |
| | | .06 | 90 | 70 | 10 | 0 | 80 | 100 | 100 | 20 | | 75 | 80 | 60 | | 50 | 20 |
| | | .03 | 90 | 40 | 0 | 0 | 35 | 85 | 90 | 70 | | 55 | 70 | 0 | 20 | 30 | 30 |
| | | .015 | 70 | 10 | 0 | 0 | 90 | 100 | 70 | 20 | | 15 | 70 | 0 | | 0 | 0 |
| | | .25 | 100 | 70 | 50 | 40 | 90 | 85 | 100 | 90 | | 0 | 90 | 100 | 50 | 0 | 100 |
| | | .12 | 90 | 60 | 20 | 20 | 80 | 100 | 100 | 80 | | 80 | 80 | 100 | 0 | 0 | 80 |
| | | .06 | 90 | 30 | 0 | 0 | 70 | 90 | 100 | 65 | | 70 | 80 | 100 | 40 | 90 | 70 |
| | | .03 | 80 | 10 | 0 | 0 | 100 | 90 | 30 | 50 | | 30 | 100 | 80 | 20 | 80 | 10 |
| | POST | .25 | 100 | 50 | 10 | 40 | 100 | 100 | 100 | 80 | | 80 | 100 | 95 | 100 | 100 | 65 |
| | | .12 | 100 | 50 | 0 | 0 | 90 | 100 | 95 | 60 | | 65 | 100 | 90 | 80 | 90 | 20 |
| | | .06 | | 0 | 0 | 0 | 75 | 100 | 60 | 40 | | 30 | 80 | 50 | 65 | 50 | 0 |
| | | .03 | | 0 | 0 | 0 | 30 | 95 | 10 | 20 | | 20 | 70 | 20 | 20 | 20 | 0 |
| (B-23) | PRE | .25 | 100 | 90 | 20 | 30 | 90 | 100 | 100 | 90 | 90 | 90 | 100 | 100 | 100 | 100 | 80 |
| | | .125 | 90 | 55 | 5 | 0 | 90 | 100 | 100 | 80 | 90 | 60 | 100 | 95 | 100 | 100 | 70 |
| | | .06 | 90 | 20 | 0 | 0 | 80 | 100 | 100 | 65 | 85 | 30 | 80 | 50 | 0 | 0 | 0 |
| | | .03 | 80 | 10 | 0 | 0 | 60 | 90 | 90 | 10 | 65 | 20 | 80 | 20 | 15 | 80 | 60 |
| (B-24) | PRE | .25 | 100 | 90 | 30 | 50 | 100 | 100 | 100 | 90 | 100 | 80 | 100 | 100 | 100 | 100 | 80 |
| (B-25) | POST | .25 | 100 | 65 | 30 | 20 | 95 | 100 | 100 | 70 | 100 | 75 | 100 | 95 | 55 | 100 | 70 |
| (B-26) | POST | .25 | 90 | 10 | 0 | 10 | 60 | 100 | 100 | 65 | 80 | 0 | 40 | 65 | 100 | 90 | 0 |
| | PRE | .1 | 100 | 30 | 15 | 35 | 85 | 90 | 30 | 0 | 95 | 65 | 100 | 0 | 90 | 0 | 60 |
| (B-27) | POST | .1 | 60 | 0 | 0 | 0 | 0 | 40 | 0 | 60 | 20 | 75 | 80 | 0 | 15 | 10 | 0 |
| | PRE | .01 | 100 | 50 | 10 | 0 | 90 | 100 | 80 | 10 | 100 | 0 | 30 | 10 | 50 | 90 | 60 |
| | POST | .01 | 40 | 10 | 0 | 0 | 70 | 40 | 100 | 60 | 70 | 20 | 60 | 90 | 80 | 100 | 0 |
| (B-28) | PRE | .1 | 90 | 30 | 10 | 10 | 100 | 100 | 100 | 70 | 95 | 80 | 80 | 90 | 90 | 100 | 70 |
| | PRE | .25 | 100 | 20 | 40 | 50 | 100 | 100 | 100 | 100 | 100 | 70 | 90 | 90 | 20 | 100 | 70 |
| | POST | .125 | 80 | 60 | 20 | 10 | 90 | 100 | 100 | 80 | 95 | 80 | 80 | 100 | 20 | 80 | 30 |
| | | .06 | 80 | 0 | 0 | 0 | 80 | 100 | 100 | 80 | 100 | 30 | 70 | 100 | 0 | 80 | 0 |

TABLE 6-continued

PRIMARY SCREENING (Herbicide)

| KSC CHEM. NO. REF. | TYPE | kg/ha | LYPES | TRZAW | GLXMX | ZEAMX | DACGL | UPLAND WEED SPECIES AMAVI | DIGSA | RUMJA | POLHY | AESIN | CAGHE | URYSA | PADDY WEED SPECIES ECHOR | CYPDI | ANEXE |
|---|---|---|---|---|---|---|---|---|---|---|---|---|---|---|---|---|---|
| | POST | .03 | 70 | 0 | 0 | 0 | 70 | 80 | 90 | 70 | | 10 | 50 | 100 | 0 | 80 | 0 |
| | | .25 | 100 | 65 | 30 | 30 | 100 | 100 | 100 | 100 | | 70 | 100 | 100 | 100 | 100 | 40 |
| (B-29) | PRE | .125 | 85 | 30 | 0 | 0 | 90 | 100 | 60 | 50 | | 50 | 60 | 60 | 60 | 80 | 20 |
| (B-30) | POST | .25 | 70 | 20 | 0 | 0 | 30 | 85 | 50 | 30 | | 0 | 60 | 30 | 30 | 30 | 0 |
| | PRE | .06 | 60 | 0 | 0 | 0 | 30 | 100 | 0 | 0 | | 0 | 60 | 20 | 20 | 0 | 0 |
| | | .03 | 100 | 85 | 30 | 80 | 100 | 100 | 100 | 90 | 90 | 85 | 100 | 90 | 85 | 100 | 30 |
| (B-31) | PRE | .25 | 100 | 75 | 30 | 25 | 100 | 100 | 100 | 100 | 100 | 90 | 100 | 100 | 100 | 100 | 60 |
| | | .125 | 100 | 90 | 30 | 40 | 100 | 100 | 100 | 90 | 80 | 80 | 90 | | | | |
| | | .06 | 90 | 30 | 0 | 0 | 90 | 100 | 100 | 70 | 70 | 40 | 90 | | | | |
| | | .03 | 65 | 15 | 0 | 0 | 60 | 60 | 40 | 60 | 25 | 0 | 25 | | | | |
| (B-32) | PRE | .25 | 100 | 70 | 40 | 50 | 100 | 100 | 100 | 90 | | 90 | 90 | 100 | 90 | 100 | 90 |
| | | .125 | 100 | 40 | 20 | 10 | 80 | 90 | 100 | 80 | | 40 | 80 | 100 | 50 | 80 | 40 |
| | | .06 | 80 | 30 | 0 | 0 | 80 | 80 | 90 | 80 | | 20 | 70 | 100 | 20 | 80 | 0 |
| | | .03 | 100 | 0 | 0 | 0 | 70 | 70 | 80 | 70 | | 0 | 40 | 50 | 0 | 50 | 0 |
| | POST | .25 | 100 | 65 | 35 | 55 | 100 | 100 | 100 | 85 | | 80 | 100 | 55 | 80 | 100 | 50 |
| | | .125 | 90 | 30 | 10 | 0 | 80 | 100 | 100 | 75 | | 60 | 90 | 10 | 30 | 70 | 40 |
| | | .06 | 70 | 20 | 0 | 0 | 70 | 100 | 100 | 40 | | 30 | 65 | 0 | 20 | 60 | 50 |
| | | .03 | 50 | 0 | 0 | 0 | 20 | 85 | 65 | 20 | | 10 | 60 | 0 | 0 | 50 | 30 |
| (B-33) | PRE | .25 | 100 | 70 | 40 | 50 | 100 | 100 | 100 | 80 | | 90 | 90 | 100 | 50 | 100 | 0 |
| | | .125 | 90 | 40 | 10 | 20 | 90 | 90 | 100 | 70 | | 50 | 80 | 100 | 40 | 100 | 20 |
| | | .06 | 80 | 10 | 0 | 0 | 80 | 80 | 100 | 80 | | 0 | 40 | 100 | 30 | 80 | 20 |
| | | .03 | 70 | 0 | 0 | 0 | 70 | 80 | 80 | 70 | | 0 | 30 | 80 | 0 | 60 | 0 |
| | POST | .25 | 100 | 75 | 40 | 65 | 100 | 90 | 100 | 100 | 100 | 75 | 100 | 100 | 95 | 100 | 40 |
| | | .125 | 85 | 30 | 10 | 0 | 80 | 90 | 65 | 65 | 100 | 55 | 100 | 80 | 60 | 60 | 30 |
| | | .06 | 75 | 10 | 0 | 0 | 40 | 80 | 20 | 40 | 65 | 20 | 50 | 20 | 20 | 60 | 0 |
| | | .03 | 55 | 0 | 0 | 0 | 20 | 80 | 20 | 10 | 40 | 0 | 0 | 0 | 0 | 60 | 0 |
| (B-34) | PRE | .25 | 100 | 90 | 45 | 50 | 90 | 90 | 100 | 65 | 100 | 100 | 100 | 100 | 80 | 90 | 60 |
| (B-35) | POST | .25 | 100 | 90 | 75 | 60 | 100 | 100 | 100 | 100 | 100 | 100 | 100 | 100 | 100 | 100 | 35 |
| (B-36) | PRE | .25 | 100 | 65 | 30 | 40 | 70 | 90 | 100 | 60 | 100 | 90 | 90 | 100 | 80 | 95 | 70 |
| (B-37) | POST | .25 | 100 | 60 | 65 | 30 | 100 | 80 | 100 | 100 | 100 | 100 | 100 | 100 | 100 | 100 | 60 |
| (B-38) | PRE | .25 | 100 | 65 | 35 | 25 | 90 | 90 | 100 | 65 | 100 | 95 | 95 | 90 | 90 | 90 | 60 |
| | POST | .25 | 100 | 70 | 30 | 30 | 90 | 100 | 100 | 100 | 100 | 90 | 100 | 100 | 90 | 100 | 90 |
| | PRE | .25 | 100 | 90 | 70 | 55 | 100 | 100 | 100 | 100 | 100 | 100 | 100 | 100 | 100 | 100 | 70 |
| (B-39) | PRE | .25 | 100 | 90 | 40 | 70 | 80 | 90 | 100 | 80 | 100 | 100 | 95 | 100 | 95 | 100 | BEI 70 |
| | POST | .25 | 100 | 65 BE | 10 | 10 | 90 | 100 | 100 | 100 | 90 | 80 | 100 | 100 | 100 | 100 | 65 |
| | PRE | .25 | 100 | 10 | 10 | 0 | 90 | 100 | 100 | 90 | 90 | 70 | 80 | 100 | 80 | 100 | 60 |
| | POST | .25 | 90 | 10 | 0 | 0 | 80 | 100 | 80 | 70 | | 0 | 100 | 90 | 100 | 100 | 20 |

TABLE 6-continued

PRIMARY SCREENING (Herbicide)

| KSC CHEM. NO. REF. | TYPE | kg/ha | UPLAND WEED SPECIES | | | | | | | | | | | | | PADDY WEED SPECIES | | | |
|---|---|---|---|---|---|---|---|---|---|---|---|---|---|---|---|---|---|---|---|
| | | | LYPES | TRZAW | GLXMX | ZEAMX | DACGL | AMAVI | DIGSA | RUMJA | POLHY | AESIN | CAGHE | URYSA | ECHOR | CYPDI | ANEXE |
| (B-40) | PRE | .25 | 90 | 10 | 0 | 0 | 70 | 100 | 90 | 65 | 90 | 20 | 75 | 15 | 20 | 10 | 10 |
| | POST | .25 | 90 | 0 | 0 | 0 | 60 | 20 | 60 | 30 | 75 | 20 | 70 | 70 | 65 | 0 | 15 |
| (B-41) | PRE | .25 | 100 | 80 | 65 | 55 | 80 | 100 | 100 | 70 | 90 | 100 | 100 | 100 | 100 | 100 | 70 |
| | POST | .25 | 100 | 70 | 35 | 10 | 90 | 100 | 100 | 90 | 100 | 85 | 100 | 100 | 100 | 100 | 60 |
| (B-42) | PRE | .25 | 100 | 90 | 40 | 60 | 90 | 100 | 100 | 90 | 100 | 80 | 100 | 90 | 100 | 90 | 80 |
| | POST | .25 | 100 | 50 | 35 | 25 | 100 | 100 | 100 | 90 | 100 | 70 | 100 | 100 | 100 | 90 | 70 |
| (B-43) | PRE | .25 | 100 | 70 | | 30 | 95 | 75 | 100 | 100 | | 90 | 100 | 90 | 100 | 90 | 90 |
| | POST | .25 | 100 | 65 | 15 | 0 | 80 | 100 | 100 | 75 | | 70 | 90 | 100 | 90 | 100 | 60 |
| (B-44) | PRE | .25 | 90 | 65 | 40 | 50 | 90 | 90 | 90 | 80 | | 70 | 60 | 100 | 50 | 100 | 60 |
| | | .125 | 80 | 20 | 10 | 5 | 80 | 100 | 60 | 70 | | 0 | 30 | 100 | 0 | 100 | 40 |
| | | .06 | 65 | 10 | 0 | 0 | 70 | 90 | 55 | 70 | | 0 | 0 | 100 | 0 | 100 | 10 |
| | | .03 | | 0 | 0 | 0 | 40 | 70 | | 60 | | 0 | 0 | | 0 | BECA | 0 |
| | POST | .25 | 95 | 20 | 20 | 10 | 95 | 100 | 60 | 70 | | 50 | 95 | 100 | 95 | 95 | 55 |
| | | .125 | 90 | 10 | B | A | 90 | 95 | 60 | 50 | | 60 | 80 | 75 | 20 | 90 | 10 |
| | | .06 | 75 | 0 | 0 | 0 | 50 | 90 | 65 | 30 | | 40 | 50 | 50 | 0 | 60 | 0 |
| | | .03 | 60 | 0 | 0 | 0 | 20 | 70 | 40 | 20 | | 20 | 50 | 40 | 0 | 50 | 0 |
| (B-45) | PRE | .25 | 100 | 60 | 45 | 30 | 100 | 100 | 100 | 100 | | 80 | 100 | 100 | 100 | 100 | 70 |
| | POST | .25 | 100 | 60 | 25 | 30 | 100 | 100 | 100 | 70 | | 90 | 100 | 100 | 100 | 100 | 60 |
| (B-46) | PRE | .25 | 100 | 85 | 55 | 90 | 100 | 100 | 100 | 100 | | 80 | 100 | 90 | 100 | 100 | 65 |
| | POST | .25 | 100 | 60 | 20 | 10 | 100 | 100 | 100 | 90 | | 90 | 100 | | | | |
| (B-47) | PRE | .25 | 90 | 60 | 15 | 15 | 90 | 90 | 100 | 75 | | 80 | 90 | 90 | 100 | 100 | 90 |
| | POST | .25 | 100 | 30 | 10 | 0 | 100 | 95 | 100 | 90 | | 80 | 90 | 90 | 100 | 100 | 70 |
| (B-48) | PRE | .25 | 80 | 70 | 10 | 0 | 90 | 100 | 100 | 70 | 100 | 70 | 90 | 90 | 100 | 100 | 35 |
| | POST | .25 | 70 | 0 | 35 | 0 | 100 | 95 | 100 | 70 | 100 | 90 | 70 | 60 | 90 | 90 | 50 |
| (B-49) | PRE | .25 | 90 | 35 | 0 | 0 | 60 | 100 | 35 | 35 | 75 | 10 | 70 | 60 | 50 | 70 | 60 |
| | POST | .25 | 100 | 70 | 30 | 30 | 80 | 90 | 100 | 60 | | 30 | 80 | 100 | 90 | 90 | 40 |
| (B-50) | PRE | .25 | 100 | 60 | 15 | 60 | 100 | 100 | 100 | 80 | 95 | 75 | 95 | 80 | 50 | 90 | 30 |
| | POST | .25 | 100 | 90 | 50 | 20 | 80 | 90 | 100 | 50 | 95 | 90 | 100 | 100 | 70 | 80 | 70 |
| (B-51) | PRE | .25 | 100 | 65 | 30 | 0 | 100 | 100 | 100 | 90 | 100 | 90 | 95 | 80 | 70 | 90 | 60 |
| | POST | .25 | 80 | 20 | 10 | 0 | 80 | 80 | 100 | 50 | | 40 | 50 | 100 | 100 | 100 | 70 |
| (B-52) | PRE | .125 | 80 | 10 | 0 | 0 | 70 | 80 | 70 | 50 | | 0 | 40 | 100 | 70 | 80 | 30 |
| | | .06 | 70 | 10 | 0 | 0 | 70 | 65 | 60 | 40 | | 0 | 20 | 100 | 0 | 70 | 0 |
| | | .03 | 60 | 0 | 0 | 0 | 65 | 30 | 30 | 90 | | 70 | 10 | 100 | 95 | 100 | 0 |
| | POST | .25 | 100 | 30 | 30 | 30 | 100 | 100 | 100 | 0 | | 0 | 100 | 0 | 0 | 0 | 60 |
| | | .125 | 20 | 20 | 0 | 0 | 10 | 20 | 0 | 0 | | 0 | 0 | 0 | 0 | 0 | 0 |
| | | .06 | 0 | 0 | 0 | 0 | 0 | 0 | 0 | 0 | | 0 | 0 | 0 | 0 | 0 | 0 |
| | | .03 | 0 | 0 | 0 | 0 | 0 | 0 | 0 | 0 | | 0 | 0 | 0 | 0 | 0 | 0 |
| (B-53) | PRE | .25 | 100 | 70 | 60 | 75 | 100 | 100 | 100 | 100 | | 90 | 90 | 90 | 100 | 100 | 60 |
| | POST | .25 | 100 | 40 | 30 | 0 | 100 | 100 | 100 | 90 | 95 | 65 | 100 | | | | |
| (B-54) | PRE | .125 | 100 | 90 | 35 | 30 | 100 | 100 | 100 | 80 | 90 | 90 | 90 | | 100 | | 80 |
| | | .06 | 100 | 60 | 5 | 20 | 90 | 100 | 75 | 50 | 80 | 65 | 90 | 90 | | | |
| | | .03 | 90 | 25 | 0 | 0 | 70 | 100 | 100 | 30 | 70 | 30 | 90 | | | | |
| (B-55) | PRE | .25 | 100 | 10 | 0 | 0 | 65 | 100 | 75 | 90 | 95 | 10 | 60 | | | | 0 |
| | | .125 | 100 | 90 | 50 | 60 | 100 | 100 | 100 | 80 | 90 | 90 | 100 | | | | 0 |
| | | .06 | 90 | 60 | 0 | 0 | 90 | 90 | 100 | 80 | 80 | 70 | 90 | | | | 0 |

TABLE 6-continued

PRIMARY SCREENING (Herbicide)

| KSC CHEM. NO. REF. | TYPE | kg/ha | UPLAND WEED SPECIES ||||||||||| PADDY WEED SPECIES |||||
|---|---|---|---|---|---|---|---|---|---|---|---|---|---|---|---|---|---|---|
| | | | LYPES | TRZAW | GLXMX | ZEAMX | DACGL | AMAVI | DIGSA | RUMJA | POLHY | AESIN | CAGHE | URYSA | ECHOR | CYPDI | ANEXE |
| (B-56) | PRE | .03 | 80 | 10 | 0 | 0 | 60 | 10 | 30 | 5 | 65 | 0 | 60 | 80 | 95 | 100 | 10 |
| | POST | .25 | 100 | 90 | 20 | 35 | 85 | 100 | 100 | 90 | 100 | 75 | 100 | 95 | 100 | 100 | 70 |
| (B-57) | PRE | .25 | 100 | 20 | 10 | 0 | 90 | 90 | 100 | 75 | 95 | 70 | 90 | | | | |
| | POST | .25 | 90 | 35 | 15 | 20 | 80 | 100 | 100 | 70 | | 70 | 100 | 90 | 80 | 100 | 55 |
| (B-58) | PRE | .25 | 100 | 30 | 15 | 0 | 80 | 90 | 100 | 80 | | 40 | 90 | 70 | 100 | 100 | 90 |
| | POST | .25 | 100 | 60 | 25 | 70 | 100 | 100 | 100 | 65 | | 70 | 100 | 100 | 100 | 100 | 80 |
| (B-59) | PRE | .25 | 100 | 30 | 35 | 0 | 100 | 90 | 100 | 90 | | 90 | 100 | 100 | 40 | 50 | 30 |
| | POST | .25 | 100 | 70 | 25 | 40 | 90 | 100 | 100 | 70 | | 90 | 100 | 100 | 100 | 100 | 40 |
| | PRE | .06 | 90 | 0 | 0 | 0 | 70 | 60 | 90 | 40 | | 40 | 70 | 10 | 40 | 10 | 10 |
| | POST | .25 | 100 | 70 | 65 | 15 | 100 | 100 | 100 | 100 | 100 | 95 | 100 | 100 | 80 | 100 | 70 |
| (B-60) | PRE | .25 | 80 | 20 | 60 | 70 | 70 | 100 | 70 | 45 | 90 | 15 | 90 | 10 | 80 | 10 | 70 |
| | POST | .25 | 100 | 80 | 30 | 0 | 100 | 100 | 100 | 90 | 100 | 90 | 100 | 100 | 100 | 100 | 90 |
| (B-61) | PRE | .25 | 100 | 75 | 30 | 20 | 100 | 100 | 100 | 80 | 90 | 70 | 100 | 100 | 100 | 100 | 70 |
| | | .125 | 90 | 50 | 20 | 0 | 100 | 100 | 100 | 80 | | 40 | 80 | 100 | 80 | 100 | 70 |
| | | .06 | 90 | 30 | 10 | 0 | 80 | 80 | 100 | 80 | | 70 | 70 | 100 | 0 | 100 | 40 |
| | | .03 | 70 | 20 | 0 | 0 | 85 | 100 | 70 | 30 | | 40 | 60 | 100 | 0 | 80 | 20 |
| | POST | .25 | 100 | 30 | 20 | 10 | 75 | 100 | 95 | 0 | | 0 | 20 | 100 | 0 | 100 | 0 |
| | | .125 | 95 | 20 | 0 | 0 | 30 | 100 | 90 | 0 | | 75 | 100 | 100 | 95 | 75 | 65 |
| | | .06 | 60 | 10 | 0 | 0 | 20 | 90 | 50 | 0 | | 40 | 95 | 100 | 60 | 60 | 20 |
| | | .03 | 55 | 0 | 0 | 0 | 20 | 65 | 30 | 0 | | 0 | 60 | 65 | 45 | 70 | 0 |
| (B-62) | PRE | .25 | 100 | 70 | 50 | 60 | 100 | 100 | 100 | 80 | 80 | 80 | 80 | 100 | 20 | 100 | 60 |
| | | .125 | 80 | 50 | 20 | 10 | 90 | 90 | 100 | 80 | | 40 | 70 | 100 | 60 | 100 | 40 |
| | | .06 | 80 | 20 | 0 | 0 | 90 | 80 | 100 | 70 | | 0 | 60 | 100 | 30 | 80 | 0 |
| | | .03 | 80 | 0 | 0 | 0 | 90 | 80 | 90 | 65 | | 70 | 40 | 100 | 30 | 100 | 0 |
| | POST | .25 | 100 | 40 | 20 | 10 | 30 | 85 | 40 | 65 | | 60 | 20 | 90 | 0 | 80 | 50 |
| | | .125 | 80 | 20 | 10 | 0 | 20 | 80 | 60 | 70 | | 20 | 50 | 75 | 100 | 100 | 50 |
| | | .06 | 60 | 10 | 0 | 0 | 20 | 80 | 40 | 20 | | 0 | 50 | 60 | 65 | 90 | 30 |
| (B-63) | PRE | .25 | 100 | 65 | 15 | 10 | 70 | 100 | 100 | 70 | | 40 | 90 | 100 | 60 | 100 | 15 |
| (B-64) | POST | .25 | 100 | 45 | 10 | 0 | 70 | 100 | 70 | 70 | | 55 | 100 | 100 | 70 | 100 | 60 |
| (B-65) | PRE | .25 | 100 | 85 | 50 | 65 | 90 | 100 | 100 | 70 | 100 | 100 | 100 | 100 | 100 | 100 | 80 |
| | POST | .25 | 100 | 60 | 55 | 55 | 100 | 100 | 100 | 100 | 100 | 90 | 100 | 90 | 100 | 100 | 40 |
| (B-66) | PRE | .25 | 100 | 90 | 55 | 65 | 100 | 100 | 100 | 70 | 100 | 90 | 100 | 100 | 100 | 100 | 30 |
| | POST | .25 | 100 | 70 | 30 | 45 | 100 | 100 | 100 | 100 | 100 | 100 | 100 | 100 | 100 | 100 | 30 |
| (B-67) | PRE | .25 | 100 | 80 | 60 | 40 | 100 | 100 | 100 | 65 | 100 | 90 | 100 | 100 | 100 | 100 | 80 |
| | POST | .25 | 100 | 85 | 45 | 50 | 100 | 100 | 100 | 100 | 100 | 90 | 100 | 100 | 100 | 100 | 85 |
| | PRE | .06 | 90 | 20 | 10 | 60 | 55 | 100 | 100 | 20 | 100 | 80 | 100 | 70 | 65 | 90 | 85 |
| (B-68) | POST | .25 | 100 | 70 | 60 | 0 | 100 | 100 | 100 | 100 | 100 | 60 | 100 | 60 | 100 | 100 | 30 |
| | PRE | .06 | 90 | 30 | 0 | 35 | 90 | 100 | 90 | 90 | 100 | 100 | 100 | 90 | 70 | 100 | 10 |
| | | .25 | 90 | 70 | 65 | 80 | 90 | 100 | 100 | 90 | 90 | 70 | 100 | 100 | 90 | 100 | 30 |
| | | .125 | 100 | 85 | 30 | 35 | 70 | 90 | 100 | 90 | 90 | 90 | 80 | 50 | 40 | 90 | 50 |
| | | | 90 | 65 | 15 | 5 | 70 | 100 | 100 | 90 | | 25 | | | | 75 | 15 |
| | | | | | | B | | | | | | | | | | | |
| | | .06 | 90 | 25 | 0 | 0 | 60 | 90 | 90 | 80 | 90 | 20 | 80 | 10 | 0 | 0 | 0 |
| | | .03 | 80 | 15 | 0 | 0 | 20 | 60 | 60 | 25 | 80 | 0 | 60 | 0 | 0 | 0 | 0 |
| | | .015 | 65 | 0 | 0 | 0 | 0 | 0 | 10 | 0 | 15 | 0 | 35 | 0 | 0 | 0 | 0 |
| | POST | .25 | 100 | 60 | 20 | 10 | 65 | 100 | 85 | 75 | 100 | 65 | 100 | 90 | 80 | 75 | 20 |

TABLE 6-continued

PRIMARY SCREENING (Herbicide)

| KSC CHEM. NO. REF. | TYPE | kg/ha | UPLAND WEED SPECIES |||||||||||||| PADDY WEED SPECIES ||||
|---|---|---|---|---|---|---|---|---|---|---|---|---|---|---|---|---|---|---|---|
| | | | LYPES | TRZAW | GLXMX | ZEAMX | DACGL | AMAVI | DIGSA | RUMJA | POLHY | AESIN | CAGHE | URYSA | ECHOR | CYPDI | ANEXE |
| (B-69) | PRE | .125 | 90 | 15 | 10 | 0 | 60 | 100 | 75 | 55 | 100 | 30 | 100 | 70 | 60 | 0 | 10 |
| | POST | .06 | 70 | 0 | 0 | 0 | 20 | 50 | 50 | 40 | 100 | 0 | 60 | 55 | 40 | 0 | 0 |
| (B-70) | PRE | .25 | 100 | 55 | 0 | 0 | 0 | 20 | 0 | 0 | 70 | 15 | 50 | 15 | 0 | 0 | 0 |
| | POST | .25 | 100 | 50 | 20 | 0 | 70 | 85 | 100 | 60 | 80 | 60 | 80 | 10 | 30 | 50 | 10 |
| (B-71) | PRE | .25 | 40 | 10 | 0 | 0 | 80 | 25 | 40 | 20 | 100 | 0 | 25 | 10 | 80 | 60 | 30 |
| | POST | .25 | 80 | 10 | 10 | 0 | 10 | 90 | 70 | 60 | | 25 | 65 | 80 | 0 | 0 | 0 |
| (B-72) | PRE | .25 | 80 | 15 | 0 | 0 | 70 | 80 | 100 | 90 | 80 | 25 | 90 | 10 | 60 | 40 | 10 |
| | POST | .25 | 90 | 0 | 25 | 80 | 65 | 100 | 70 | 70 | 90 | 80 | 90 | 70 | 0 | 70 | 0 |
| (B-73) | PRE | .25 | 100 | 80 | 60 | 0 | 100 | 100 | 100 | 90 | | 80 | 100 | 90 | 65 | 0 | 0 |
| | POST | .25 | 100 | 10 | 15 | 50 | 90 | 100 | 100 | 70 | | 70 | 85 | | 80 | 100 | 60 |
| (B-74) | PRE | .25 | 100 | 70 | 40 | 15 | 90 | 100 | 100 | 80 | | 75 | 100 | 90 | 90 | 100 | 90 |
| | POST | .25 | 100 | 60 | 50 | 70 | 90 | 100 | 100 | 100 | 100 | 70 | 100 | 100 | 100 | 90 | 70 |
| (B-75) | PRE | .25 | 100 | 90 | 65 | 20 | 100 | 100 | 100 | 90 | 100 | 100 | 100 | 100 | 100 | 90 | 60 |
| | POST | .25 | 100 | 85 | 55 | 15 | 100 | 100 | 100 | 100 | 100 | 90 | 100 | 100 | 100 | 100 | 60 |
| (B-76) | PRE | .25 | 100 | 80 | 30 | 20 | 85 | 100 | 100 | 80 | 100 | 100 | 100 | 95 | 100 | 100 | 60 |
| | POST | .25 | 100 | 65 | 10 | 0 | 100 | 100 | 100 | 70 | 95 | 85 | 100 | 100 | 100 | 100 | 65 |
| (B-77) | PRE | .25 | 100 | 90 | 70 | 70 | 90 | 100 | 100 | 100 | 100 | 100 | 100 | 100 | 100 | 100 | 90 |
| | POST | .25 | 100 | 65 | 50 | 30 | 100 | 100 | 100 | 100 | 100 | 90 | 100 | 90 | 80 | 100 | 60 |
| (B-78) | PRE | .25 | 100 | 90 | 30 | 60 | 100 | 100 | 100 | 100 | 100 | 80 | 100 | 100 | 100 | 100 | 70 |
| | POST | .25 | 100 | 70 | 30 | 30 | 80 | 100 | 100 | 40 | 100 | 100 | 100 | 100 | 100 | 100 | 70 |
| (B-79) | PRE | .25 | 90 | 50 | 20 | 0 | 100 | 100 | 100 | 85 | 95 | 75 | 100 | 100 | 80 | 95 | 70 |
| | POST | .25 | 100 | 80 | 60 | 90 | 100 | 100 | 100 | 80 | 100 | 90 | 100 | 100 | 100 | 100 | 70 |
| (C-1) | PRE | .5 | 100 | 70 | 65 | 30 | 35 | 90 | 100 | 90 | 100 | 10 | 90 | 90 | 80 | 95 | 65 |
| | | .25 | 90 | 85 | 0 | 10 | 20 | 90 | 90 | 15 | 90 | 0 | 90 | 90 | 70 | 100 | 70 |
| | | .125 | 70 | 70 | 0 | 0 | 20 | 90 | 90 | 0 | 90 | 0 | 60 | 80 | 50 | | 50 |
| | | .06 | 65 | 25 | 0 | 0 | 0 | 85 | 80 | 0 | 90 | 0 | 60 | 65 | 50 | | 15 |
| | POST | .5 | | 0 | 0 | 0 | 0 | | | | | | | | | | – |
| (C-2) | POST | .5 | 100 | 90 | 0 | 65 | 70 | 70 | 90 | 65 | 90 | 25 | 90 | 90 | 90 | 100 | 80 |
| (C-3) | PRE | .25 | 90 | 60 | 0 | 0 | 60 | 70 | 90 | 50 | 90 | 10 | 80 | 90 | 90 | 100 | 70 |
| | POST | .25 | 80 | 15 | 0 | 0 | 60 | 70 | 70 | 15 | 90 | 0 | 80 | 80 | 85 | 90 | 35 |
| (C-4) | PRE | .125 | 60 | 0 | 0 | 0 | 35 | 55 | 70 | 0 | 70 | 0 | 40 | 65 | 70 | 80 | 10 |
| | POST | .06 | 60 | 60 | 0 | 30 | 60 | 90 | 100 | 50 | 70 | 10 | 80 | 90 | 55 | 50 | 10 |
| (C-5) | PRE | .25 | 70 | 10 | 0 | 0 | 55 | 90 | 65 | 10 | 80 | 0 | 30 | 60 | 70 | 80 | 50 |
| | POST | .25 | 90 | 20 | 0 | 0 | 30 | 90 | 90 | 10 | 80 | 0 | 60 | 100 | 90 | 40 | 15 |
| (C-6) | PRE | .25 | 80 | 10 | 0 | 20 | 70 | 80 | 80 | 60 | 80 | 0 | 35 | 70 | 80 | 80 | 50 |
| | POST | .25 | 100 | 15 | 15 | 15 | 70 | 90 | 90 | 40 | 80 | 0 | 95 | 80 | 70 | 80 | 10 |
| (C-7) | PRE | .25 | 70 | 70 | 0 | 10 | 90 | 80 | 100 | 70 | 70 | 0 | 100 | 70 | 90 | 100 | 70 |
| | POST | .25 | 100 | 60 | 0 | 10 | 60 | 90 | 90 | 35 | 80 | 10 | 80 | 70 | 100 | 60 | 25 |
| (C-8) | PRE | .25 | 70 | 10 | 0 | 0 | 50 | 80 | 100 | 20 | 70 | 0 | 65 | 70 | 100 | 60 | 60 |
| | POST | .25 | 95 | 40 | 20 | 10 | 40 | 90 | 90 | 25 | 70 | 0 | 70 | 80 | 30 | 60 | 70 |
| (C-9) | PRE | .25 | 80 | 60 | 0 | 0 | 65 | 100 | 65 | 15 | 75 | 0 | 100 | 100 | 100 | 50 | 20 |
| | POST | .25 | 90 | 35 | 10 | 0 | 20 | 90 | 100 | 0 | 70 | 0 | 85 | 70 | 60 | 90 | 15 |
| | | | | | | | | | | | | | 100 | | 80 | 20 | 0 |

TABLE 6-continued

PRIMARY SCREENING (Herbicide)

| KSC CHEM. NO. REF. | TYPE | kg/ha | UPLAND WEED SPECIES ||||||||||| PADDY WEED SPECIES ||||
|---|---|---|---|---|---|---|---|---|---|---|---|---|---|---|---|---|---|
| | | | LYPES | TRZAW | GLXMX | ZEAMX | DACGL | AMAVI | DIGSA | RUMJA | POLHY | AESIN | CAGHE | URYSA | ECHOR | CYPDI | ANEXE |
| (C-10) | PRE | .25 | 100 | 40 | 0 | 15 | 65 | 90 | 100 | 80 | | 0 | 80 | 100 | 80 | 90 | 20 |
| | POST | .25 | 100 | 40 | 10 | 10 | 65 | 100 | 90 | 40 | 90 | 0 | 100 | 100 | 100 | 100 | 30 |
| (C-11) | PRE | .25 | 100 | 70 | 0 | 25 | 70 | 90 | 100 | 85 | | 0 | 70 | 100 | 100 | 90 | 50 |
| | POST | .25 | 100 | 70 | 0 | 30 | 60 | 100 | 100 | 70 | 90 | 0 | 100 | 100 | 90 | 100 | 20 |
| (C-12) | PRE | .25 | 90 | 75 | 0 | 10 B | 70 | 90 | 100 | 60 | 90 | 0 | 100 | 100 | 95 | 90 | 70 |
| (C-13) | POST | .25 | 100 | 70 | 0 | 10 | 65 | 100 | 85 | 20 | 80 | 10 | 90 | 70 | 100 | 80 | 60 |
| | PRE | .25 | 90 | 20 | 10 | 0 | 60 | 90 | 85 | 35 | 70 | 0 | 60 | 75 | 70 | 90 | 0 |
| (C-14) | PRE | .25 | 80 | 15 | 10 | 0 | 20 | 100 | 70 | 10 | 60 | 0 | 60 | 30 | 65 | 0 | 0 |
| | POST | .25 | 100 | 60 | 0 | 20 | 85 | 90 | 100 | 90 | | 0 | 95 | 100 | 95 | 100 | 25 |
| (C-15) | PRE | .25 | 70 | 60 | 10 | 10 | 50 | 100 | 80 | 50 | 80 | 0 | 100 | 90 | 70 | 65 | 30 |
| | POST | .25 | 10 | 0 | 0 | 0 | 0 | 55 | 0 | 0 | 20 | 0 | 0 | 30 | 0 | 50 | 0 |
| (C-16) | PRE | .25 | 60 | 15 | 10 | 0 | 20 | 65 | 20 | 20 | | 15 | 50 | 60 | 50 | 20 | 0 |
| | POST | .25 | 20 | 0 | 0 | 0 | 0 | 100 | 50 | 0 | | 0 | 10 | 10 | 10 | 50 | 0 |
| (C-17) | PRE | .25 | 30 | 15 | 0 | 15 | 0 | 50 | 40 | 10 | 40 | 0 | 50 | 30 | 20 | 60 | 25 |
| | POST | .25 | 90 | 0 | 0 | 0 | 0 | 90 | 100 | 0 | 95 | 0 | 95 | 60 | 90 | 70 | 20 |
| (C-18) | PRE | .25 | 100 | 60 | 10 | 20 | 50 | 100 | 95 | 45 | 75 | 0 | 80 | 70 | 100 | 90 | 20 |
| | | .125 | 100 | 40 | 0 | 20 | 90 | 80 | 100 | 80 | | 0 | 80 | 100 | 60 | 70 | 60 |
| | | .06 | 80 | 20 | 0 | 0 | 90 | 80 | 100 | 70 | | 0 | 70 | 100 | 20 | 70 | 50 |
| | POST | .25 | 70 | 0 | 0 | 0 | 80 | 70 | 70 | 65 | | 0 | 60 | 100 | 0 | 70 | 30 |
| | | .125 | 100 | 10 | 0 | 0 | 30 | 100 | 60 | 60 | | 0 | 50 | 100 | 0 | 100 | 50 |
| | | .06 | 80 | 0 | 5 | 0 | 20 | 75 | 50 | 30 | | 0 | 100 | 100 | 100 | 80 | 20 |
| | | .03 | 50 | 0 | 0 | 0 | 20 | 65 | 10 | 20 | | 0 | 75 | 90 | 65 | 65 | 50 |
| | | | 30 | 0 | 0 | 0 | 0 | AB 65 | 0 | 10 | | 0 | 60 | 65 | 30 | 60 | 20 |
| | | | | | | | | | | B | | | 20 | 60 | 0 | 0 | 0 |
| (C-19) | PRE | .25 | 90 | 20 | 0 | 10 | 80 | 90 | 100 | 70 | | 15 | 80 | 100 | 90 | 90 | 70 |
| | POST | .25 | 90 | 10 | 0 | 0 | 65 | 100 | 90 | 20 | | 0 | 100 | 90 | 90 | 100 | 40 |
| (C-20) | PRE | .25 | 80 | 0 | 10 | 0 | 15 | 50 | 25 | 0 | 60 | 0 | 0 | 0 | 10 | 50 | 0 |
| | POST | .25 | 75 | 15 | 0 | 0 | 0 | 90 | 20 | 0 | 20 | 0 | 45 | 25 | 55 | 0 | 0 |
| (C-21) | PRE | .25 | 95 | 60 | 10 | 15 | 80 | 90 | 100 | 80 | 90 | 0 | 90 | 100 | 90 | 90 | 60 |
| | POST | .25 | 80 | 20 | 0 | 5 | 70 | 85 | 90 | 60 | | 0 | 80 | 90 | 100 | 100 | 60 |
| (C-22) | PRE | .25 | 100 | 50 | 5 | 0 | 100 | 90 | 100 | 80 | | 0 | 90 | 100 | 65 | 100 | 70 |
| | POST | .125 | 80 | 30 | 0 | 0 | 100 | 90 | 100 | 70 | | 15 | 70 | 100 | 40 | 100 | 40 |
| | | .06 | 70 | 10 | 0 | 0 | 90 | 80 | 65 | 60 | | 0 | 40 | 100 | 20 | 100 | 0 |
| | POST | .03 | 100 | 30 | 10 | 10 | 80 | 80 | 100 | 60 | | 0 | 10 | 90 | 10 | 90 | 50 |
| | | .25 | 75 | 20 | 0 | 10 | 50 | 95 | 80 | 40 | | 0 | 95 | 95 | 95 | 95 | 0 |
| | | .125 | 65 | 10 | 0 | 0 | 30 | 90 | 50 | 20 | | 0 | 70 | 65 | 60 | 70 | 0 |
| | | .06 | 55 | 0 | 0 | 0 | 20 | 90 | 0 | 10 | | 15 | 50 | 50 | 30 | 50 | 0 |
| | | .03 | 90 | 40 | 0 | 10 | 70 | 90 | 95 | 70 | | 0 | 45 | | 0 | | 0 |
| (C-23) | PRE | .25 | 100 | 20 | 0 | 10 | 50 | 100 | 90 | 50 | | 10 | 90 | 65 | 50 | 80 | 70 |
| (C-24) | POST | .25 | 90 | 60 | 10 | 10 | 70 | 90 | 100 | 70 | | 0 | 80 | 70 | 70 | 90 | 0 |
| (C-25) | PRE | .25 | 90 | 10 | 0 | 35 | 40 | 70 | 70 | 20 | | 0 | 100 | 100 | 100 | 90 | 65 |
| (C-26) | POST | .25 | 100 | 40 | 15 | 10 | 70 | 90 | 100 | 65 | | 0 | 80 | 100 | 60 | 100 | 85 |
| (C-27) | PRE | .25 | 85 | 30 | 0 | 10 | 65 | 80 | 100 | 35 | | 0 | 90 | 65 | | 90 | 20 |
| | POST | .25 | 90 | 15 | 0 | 0 | 30 | 90 | 90 | 55 | | 0 | 85 | | | 100 | |
| | PRE | .25 | 80 | 30 | 0 | 0 | 60 | 70 | 90 | | | 0 | | | | | |

TABLE 6-continued
PRIMARY SCREENING (Herbicide)

| KSC CHEM. NO. REF. | TYPE | kg/ha | UPLAND WEED SPECIES | | | | | | | | | | | PADDY WEED SPECIES | | | |
|---|---|---|---|---|---|---|---|---|---|---|---|---|---|---|---|---|---|
| | | | LYPES | TRZAW | GLXMX | ZEAMX | DACGL | AMAVI | DIGSA | RUMJA | POLHY | AESIN | CAGHE | URYSA | ECHOR | CYPDI | ANEXE |
| (C-28) | POST | .25 | 100 | 10 | 0 | 0 | 40 | 100 | 90 | 20 | | 0 | 90 | 90 | 100 | 100 | 30 |
| (C-28) | PRE | .25 | 90 | 30 | 5 | 5 | 90 | 100 | 100 | 90 | | 0 | 60 | 100 | 20 | 100 | 40 |
| | | .125 | 80 | 20 | 0 | 0 | 70 | 80 | 80 | 80 | | 0 | 40 | 100 | 0 | 80 | 0 |
| | | .06 | 70 | 10 | 0 | 0 | 60 | 70 | 70 | 70 | | 0 | 30 | 90 | 0 | 70 | 0 |
| | | .03 | 60 | 0 | 0 | 0 | 50 | 70 | 40 | 65 | | 0 | 0 | 80 | 0 | 70 | 20 |
| | POST | .25 | 95 | 30 | 0 | 0 | 30 | 100 | 65 | 20 | | 0 | 60 | 95 | 90 | 95 | 0 |
| | | .125 | 65 | 10 | 0 | 0 | 20 | 100 | 20 | 0 | | 0 | 50 | 80 | 40 | 65 | 0 |
| | | .06 | 40 | 0 | 0 | 0 | 0 | 60 | 0 | 0 | | 0 | 10 | 60 | 0 | 90 | 0 |
| | | .03 | 40 | 0 | 10 | 0 | 0 | 50 | 0 | 0 | | 0 | 10 | 55 | 0 | 90 | 0 |
| (C-29) | PRE | .25 | 70 | 10 | 0 | 0 | 30 | 60 | 70 | 0 | | 0 | 40 | 65 | 65 | 70 | 15 |
| (C-29) | POST | .25 | 90 | 30 | 25 | 10 | 10 | 70 | 65 | 15 | | 0 | 100 | | | | |
| (C-30) | PRE | .25 | 80 | 25 | 0 | 0 | 25 | 90 | 85 | 20 | | 0 | 70 | 55 | 25 | 60 | 0 |
| (C-30) | POST | .25 | 70 | 0 | 0 | 0 | 30 | 60 | 65 | 0 | 70 | 0 | 70 | 80 | 10 | 70 | 0 |
| (C-31) | PRE | .25 | 70 | 0 | 0 | 0 | 50 | 90 | 85 | 10 | | 0 | 60 | 70 | 50 | 20 | 10 |
| (C-31) | POST | .25 | 70 | 10 | 0 | 10 | 30 | 70 | 60 | 30 | | 30 | 55 | 60 | 70 | 90 | 30 |
| (C-32) | PRE | .25 | 90 | 40 | 0 | 0 | 100 | 100 | 100 | 70 | | 0 | 85 | 90 | 85 | 50 | 55 |
| (C-32) | POST | .25 | 80 | 15 | 25 | 0 | 50 | 70 | 100 | 50 | | 20 | 90 | 60 | 30 | 50 | 50 |
| (C-33) | PRE | .25 | 80 | 15 | 0 | 0 | 100 | 100 | 90 | 50 | | 0 | 60 | 100 | 100 | 90 | 90 |
| (C-33) | POST | .25 | 70 | 10 | 20 | 0 | 0 | 40 | 20 | 0 | | 0 | 45 | 50 | 35 | 70 | 30 |
| (D-1) | PRE | .25 | 90 | 90 | 0 | 70 | 80 | 90 | 100 | 90 | 90 | 20 | 90 | 90 | 90 | 100 | 0 |
| (D-1) | POST | .25 | 40 | 60 | 0 | 70 | 60 | 70 | 80 | 55 | 80 | 25 | 40 | 70 | 60 | 70 | 90 |
| (D-2) | PRE | .25 | 90 | 90 | 0 | 70 | 70 | 90 | 90 | 80 | 90 | 15 | 70 | 70 | 60 | 100 | 15 |
| (D-2) | POST | .25 | 40 | 60 | 0 | 80 | 75 | 70 | 60 | 70 | 80 | 10 | 65 | 100 | 65 | 70 | 70 |
| (D-3) | PRE | .25 | 90 | 90 | 0 | 65 | 70 | 70 | 90 | 90 | 70 | 0 | 90 | 70 | 70 | 90 | 10 |
| (D-3) | POST | .25 | 55 | 30 | 0 | 60 | 70 | 70 | 60 | 60 | 80 | 10 | 65 | 90 | 85 | 70 | 70 |
| (D-4) | PRE | .25 | 90 | 90 | 65 | 100 | 80 | 80 | 70 | 50 | 80 | 50 | 65 | 60 | 30 | 50 | 55 |
| (D-4) | POST | .25 | 100 | 90 | 90 | 70 | 60 | 90 | 90 | 80 | 80 | 80 | 100 | 100 | 100 | 50 | 50 |
| (D-5) | PRE | .25 | 90 | 90 | 0 | 70 | 80 | 90 | 90 | 80 | 90 | 0 | 90 | 90 | 70 | 90 | 90 |
| (D-5) | POST | .25 | 60 | 35 | 0 | 65 | 60 | 70 | 70 | 55 | 70 | 15 | 45 | 70 | 35 | 65 | 30 |

EXAMPLE 6

Wettable Powder

3-N-methyl-N-3-fluorophenylaminooxoacetyl)-2-(4-isopropyl-4-methyl-5-oxo-2-imidazolin-2 -yl)-5methyl-pyridine : 50%
sodium alkylnaphthalenesulfonate: 2%
low viscosity methyl ceollulose : 2%
diatomaceous earth : 46%

The ingredients are blended, coarsely hammer-milled and then, air milled to produce particles of active essentially all below 10 microns in diameter

EXAMPLE 7

Emulsifiable concentrate

3-N-methyl-N-3-chloro-4-methoxyphenylaminooxo-acetyl)-2-(4-isopropyl-4-methyl-5-oxo-2 -imidazolin-2-yl)-5-methylpyridine: 10%
chlorobenzene : 84% sorbitan monostearate and polyoxyethylene condensates thereof : 6%

The ingredient are combined and stirred to produce a solution which can be emulsified in water for application

EXAMPLE 8

Dust

3(N-methyl-N-3-fluorophenylaminooxoacetyl)-2-(4-isopropyl-4methyl-5-oxo-2-imidazolin-2 -yl)-5-methyl-pyridine : 10%
attapulgite : 10%
pyrophylite : 80%

The active ingredient is blended with attapulgite and then passed through a hammer-mill to produce particles substantially all below 200 microns. The ground concentrate is then blended withpowdered pyrophylite until homogeneous.

EXAMPLE 9

Granule wettable powder of Example : 6%
attapulgite granules : 95%
(U.S.S. 20–40 mesh ; 0.84~0.4 mm)

A slurry of wettable powder containing 25% solids is sprayed on the surface of attapulgite granules in a double-cone blender. The granules are dried and packaged.

What is claimed is:

1. 3-(aminooxoacetyl)-2-(2-imidazolin-2-yl)-pyridine and its salt having the structure of formula (I)

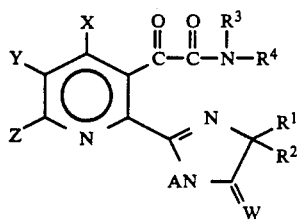

wherein,
$R^1$ is $C_1$-$C_4$ alkyl;
$R^2$ is $C_1$-$C_4$ alkyl, $C_3$-$C_5$ cycloalkyl or $C_1$-$C_4$ alkyl optionally substituted with 1-4 fluorine;
$R^3$ is hydrogen, $C_1$-$C_3$ alkyl, $C_1$-$C_3$ alkyl optionally substituted with substituents contained in the following group I, $C_2$-$C_4$ alkenyl or $C_2$-$C_4$ alkynyl;
$R^4$ is the same as $R^3$; or phenyl optionally substituted with 0-3 same or different substituents selected from the substituents contained in group II
W is O or S;
X is hydrogen, $C_1$-$C_4$ alkyl, $C_1$-$C_4$ alkoxy, $C_1$-$C_4$ alkoxyalkyl, or halogen,
Y, Z are each hydrogen, halogen, $C_1$-$C_6$ alkyl, $C_1$-$C_6$ alkoxy, $C_1$-$C_6$ alkoxyalkyl, $C_1$-$C_6$ alkylthio, phenoxy, $C_1$-$C_6$ haloalkyl, $C_1$-$C_6$ alkylamino, $C_1$-$C_6$ alkylsulfonyl or phenyl optionally substituted with one $C_1$-$C_4$ alkyl, $C_1$-$C_4$ alkoxy or halogen;
A is hydrogen or —$COR^5$ (where $R^5$ is hydrogen, methyl or $CH_2Cl$);
when A is hydrogen, tautomeric isomer may exist;
Group I contains hydroxy, $C_1$-$C_6$ alkoxy, $C_1$-$C_6$ haloalkoxy, cyano, —$CO_2R^6$ (where $R^6$ is hydrogen, $C_1$-$C_4$ alkyl, $C_2$-$C_4$ alkenyl, or $C_2$-$C_4$ alkynyl), $C_1$-$C_4$ alkylthio, $C_1$-$C_4$ alkylsulfonyl, phenylthio, phenylsulfonyl, $C_1$-$C_4$ haloalkylthio, $C_3$-$C_5$ alkenoxy, alkoxy, —$NR^6R^7$ are each hydrogen, $C_1$-$C_3$ alkyl, $C_2$-$C_3$ alkenyl or $C_1$-$C_3$ alkynyl), phenyl, or phenoxy;
Group II contains group I substituents 1-3 halogen, nitro, $C_1$-$C_6$ haloalkyl, $C_2$-$C_6$ alkoxyalkyl, $C_1$-$C_6$ alkyl, $C_2$-$C_6$ alkenyl, $C_2$-$C_6$ alkynyl, $C_2$-$C_6$ alkylthioalkyl, —$CO_2R^9$ (where $R^9$ is hydrogen or $C_1$-$C_4$ alkyl), —$SO_3R^{10}$ (where $R^{10}$ is hydrogen or $C_1$-$C_4$ alkyl), —$SO_2NR^6R^7$, —$CONR^6R^7()R^6,R^7$ are the same as above).

2. The compound according to claim 1 where $R^1$ is methyl; $R^2$ is ethyl or isopropyl; $R^3$ is hydrogen, methyl, ethyl, methoxymethyl, methylthiomethyl, or allyl, $R^4$ is $C_1$-$C_2$ alkyl optionally substituted 0-2 substituents selected from 1-3 halogen, hydroxy, $C_1$-$C_4$ alkoxy, $C_1$-$C_4$ alkylthio, $R^6$ $NR^7$ (where $R^6$, $R^7$, are hydrogen, $C_1$-$C_4$ alkyl, $C_2$-$C_4$ alkenyl, or $C_2$-$C_5$ alkynyl), phenyl, phenoxy, or phenyl optionally substituted with 0-3 same or different substituents selected from substituents contained in the above group II;
A is hydrogen; W is O; X is hydrogen,
Y is hydrogen, methyl or ethyl;
Z is hydrogen, methyl or ethyl.

3. The compound according to claim 2 where $R^2$ is ispropyl; $R^3$ is methyl or $CH_2C_3$; $R^4$ is phenyl substituted with substiuents contained in the above group II;
Y is hydrogen, methyl or ethyl.

4. The compound according to of claim 3 where $R^3$ is phenyl optionally subsituted 0-2 subsitutes selected from methyl, ethyl, propyl, isopropyl, butyl, tertbutyl, cyclohexyl, methoxy, ethothy, isopropoxy, phenoxy, $SCH_3$, $SO_2CH_3$, Cl, Br, F, $(CH_3)_2$ N and $CF_3$; Y is methyl.

5. The compound according to claim 1 having said formula(I) of 3-(N-methyl-N-3-fluorophenyl-aminooxoacetyl)-2-(4-isopropyl-4-methyl-5-oxo-2-imidazolin-2 -yl)-5-methyl-pyridine., 6. The compound according to claim 1 having said formula(I) of 3-(N-methyl-N-3-chloro-4-methoxyphenyl-aminooxoacetyl)-2-(4-isopropyl-4-methyl-5-oxo-2 -imidazolin-2-yl)-5-methyl-pyridine.

7. The compound according to claim 1 having said formula(I) pf 3-(N-methyl-N-3,5-dimethylphenyl-aminooxoacetyl)-2-(4-isopropyl-4-methyl-5-oxo-2-imidazolin-2 yl)-5-methyl-pyridine.

8. The compound according to claim 1 having said formula(I) of 3-(N-methyl-4-n-butylphenyl-aminooxoacetyl)-2-(4-isopropyl-4-methyl-5-oxo-2-imidazolin-2-yl)-5-methyl-pyridine.

9. The compound according to claim 1 having said general formula(I) of 3-(N-methyl-N-4-t-butylphenyl-aminooxoacetyl)-2-(4-isopropyl-4-methyl-5-oxo-2-imidazolin-2-yl)-5-methyl-pyridine.

10. The compound according to claim 1 having said formula(I) of 3-(N-methyl-N-4-phenoxyphenyl-aminooxoacetyl)-2-(4-isopropyl-4-methyl-5-oxo-2-imidazolin-2-yl)-5-methylpyridine.

11. The compound according to claim 1 having said general formula(I) of 3-(N-methyl-N-3-chlorophenyl-aminooxoacetyl)-2-(4-isopropyl-4-methyl-5-oxo-2-imidazolin-2-yl)-5-methyl-pyridine.

12. The compound according to claim 1 having said formula(I) of 3-(N-methyl-N-4-cyclohexylphenyl-aminooxoacetyl)-2-(4-isopropyl-4-methyl-5-oxo-2-imidazolin-2-yl)-5-methyl-pyridine.

13. The compound according to claim 1 having said formula(I) of 3-(N-methyl-N-4-dimethylamionophenyl-aminooxoacetyl)-2-(4-isopropyl-4-methyl-5-oxo-2-imidazolin-2-yl)-5-methyl-pyridine. methyl-pyridine.

14. The compound according to claim 1 having said general formula(I) of 3-(N-methyl-N-3-trifluoromethylphenyl-aminooxoacetyl)-2-(4-isopropyl-4-methyl-5-oxo-2-imidazolin-2-yl)-5-methyl-pyridine.

15. The compound according to claim 1 having said formula(I) of 3-(N-methyl-N-3,4-dichlorophenyl-aminooxoacetyl)-(4-isopropyl-4-methyl-5-oxo-2-imidazolin-2-yl)-5-methyl-pyridine.

16. The compound according to claim 1 having said formula(I) of 3-(N-methyl-N-4-trifluoromethylphenyl-aminooxoacetyl)-2-(4-isopropyl-4-methyl-5-oxo-2-imidazolin-2-yl)-5-methyl-pyridine.

17. The compound according to claim 1 having said formula(I) of 3-(N-methyl-N-3-methylphenyl-aminooxoacetyl)-2-(4-isopropyl-4-methyl-5-oxo-2-imidazolin-2-yl)-5-methyl-pyridine.

18. A herbicidal composition comprising an effective amount of the compound of claim 1 as active ingredient and a suitable carrier.

19. The composition according to claim 18, in the form of a wettable powder wherein said composition has the following formula: 45-80 wt percent active ingredient, 20-40 wt percent micro-powder carrier, 2-5 wt percent dispersing agent and 2-5 wt percent non-ionic surfactant.

20. The composition according to claim 18, in the form of a flowable liquid, wherein said composition has the following formula: 30-50 wt percent active ingredient, 1-3 wt percent gelator, 1-5 wt percent dispersing agent, 0.1-3 wt percent alcohol and 40-60 wt percent water.

21. The composition according to claim 18, in the form of an emulsified concentrate wherein said composition has the following formula: 5-25 wt percent non-ionic surfactant.

22. The composition according to claim 18, in a particle form, wherein said composition has the following formula: 3-20 wt percent active ingredient and 80-97 wt percent granular carrier.

23. A method of using the composition of claim 18, comprising the step of applying the composition to the soil in a ratio of about 0.03-10 kg/ha.

* * * * *